(12) United States Patent
Sisk et al.

(10) Patent No.: US 9,112,159 B2
(45) Date of Patent: Aug. 18, 2015

(54) BIPOLAR HOSTS FOR LIGHT EMITTING DEVICES

(71) Applicant: NITTO DENKO CORPORATION, Osaka (JP)

(72) Inventors: David T. Sisk, San Diego, CA (US); Shijun Zheng, San Diego, CA (US)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 14/102,183

(22) Filed: Dec. 10, 2013

(65) Prior Publication Data

US 2014/0163237 A1  Jun. 12, 2014

Related U.S. Application Data

(60) Provisional application No. 61/735,478, filed on Dec. 10, 2012.

(51) Int. Cl.

| C07D 413/14 | (2006.01) |
|---|---|
| C07D 235/20 | (2006.01) |
| C07D 403/10 | (2006.01) |
| C07D 403/14 | (2006.01) |
| C07D 235/18 | (2006.01) |
| H01L 51/00 | (2006.01) |
| H01L 51/50 | (2006.01) |

(52) U.S. Cl.
CPC .......... *H01L 51/0072* (2013.01); *C07D 235/18* (2013.01); *C07D 235/20* (2013.01); *C07D 403/10* (2013.01); *C07D 403/14* (2013.01); *C07D 413/14* (2013.01); *H01L 51/006* (2013.01); *H01L 51/0061* (2013.01); *H01L 51/0071* (2013.01); *H01L 51/0059* (2013.01); *H01L 51/0085* (2013.01); *H01L 51/5016* (2013.01); *H01L 51/5036* (2013.01)

(58) Field of Classification Search
None
See application file for complete search history.

(56) References Cited

U.S. PATENT DOCUMENTS

| 6,620,529 | B1 | 9/2003 | Ise et al. |
|---|---|---|---|
| 6,835,469 | B2 | 12/2004 | Kwong et al. |
| 7,332,860 | B2 | 2/2008 | Hatwar et al. |
| 7,678,959 | B2 | 3/2010 | Okada et al. |
| 8,426,040 | B2 * | 4/2013 | Zheng et al. .................. 428/690 |
| 8,929,978 | B2 * | 1/2015 | Khan et al. ....................... 604/20 |
| 2005/0106710 | A1 | 5/2005 | Friedman et al. |
| 2008/0014464 | A1 | 1/2008 | Kawamura |
| 2008/0311178 | A1 | 12/2008 | Ishikura et al. |
| 2009/0134783 | A1 | 5/2009 | Lin et al. |
| 2010/0060154 | A1 | 3/2010 | Nomura et al. |
| 2010/0060155 | A1 | 3/2010 | Seo et al. |
| 2010/0326526 | A1 | 12/2010 | Zheng |
| 2011/0127510 | A1 * | 6/2011 | Seo et al. ........................ 257/40 |
| 2011/0140093 | A1 * | 6/2011 | Zheng et al. ..................... 257/40 |
| 2011/0251401 | A1 | 10/2011 | Zheng et al. |
| 2012/0104277 | A1 | 5/2012 | Morren |
| 2012/0179089 | A1 | 7/2012 | Sisk et al. |
| 2012/0197179 | A1 * | 8/2012 | Khan et al. ....................... 604/20 |
| 2012/0223633 | A1 | 9/2012 | Yoshinaga et al. |

(Continued)

FOREIGN PATENT DOCUMENTS

| CN | 101400658 | 4/2009 |
|---|---|---|
| GB | 2408209 | 5/2005 |

(Continued)

OTHER PUBLICATIONS

International Search Report for International Application No. PCT/US2013/074154 filed on Dec. 10, 2013.
Ge, Ziyi et al. Solution-Processible Bipolar Triphenylamine-Benzimidazole Derivatives for Highly Efficient Single-Layer Organic Light-Emitting Diodes, Chemistry of Materials, American Chemical Society, Washington DC, US, vol. 20, No. 20, Apr. 8, 2008, pp. 2532-2537.
Peng et al., "5-Aminolevulinic Acid-Based Photodynamic Therapy. Clinical Research and Future Challenges", Cancer, Jun. 15, 1997, vol. 79, No. 12, pp. 2282-2308.

(Continued)

*Primary Examiner* — Michael Barker
*Assistant Examiner* — Po-Chih Chen
(74) *Attorney, Agent, or Firm* — K&L Gates LLP; Louis C. Cullman; Brent A. Johnson

(57) ABSTRACT

Some embodiments provide a compound represented by Formula 1:

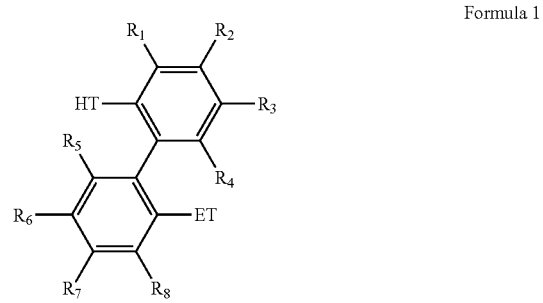

wherein $R_1$, $R_2$, $R_3$, $R_4$, $R_5$, $R_6$, $R_7$ and $R_8$ are independently H, $C_1$-$C_3$ alkyl, or $C_{1-3}$ perfluoroalkyl; HT is optionally substituted carbazoyl, optionally substituted phenylcarbazolyl, optionally substituted (phenylcarbazolyl)phenyl, optionally substituted phenylnaphthylamine, or optionally substituted diphenylamine; and ET optionally substituted benzimidazol-2-yl, optionally substituted benzothiazol-2-yl, optionally substituted benzoxazol-2-yl, optionally substituted 3,3'-bipyridin-5-yl, optionally substituted quinolin-8-yl, optionally substituted quinolin-5-yl, or optionally substituted quinoxalin-5-yl. Other embodiments provide an organic light-emitting diode device comprising a compound of Formula 1.

3 Claims, 4 Drawing Sheets

(56) References Cited

U.S. PATENT DOCUMENTS

| | | | |
|---|---|---|---|
| 2012/0223635 A1 | 9/2012 | Mochizuki et al. | |
| 2013/0140534 A1* | 6/2013 | Lai et al. | 257/40 |

FOREIGN PATENT DOCUMENTS

| | | | |
|---|---|---|---|
| WO | 2004020388 | | 3/2004 |
| WO | 2006101735 | | 9/2006 |
| WO | 2006130302 | | 12/2006 |
| WO | 2008/052350 | | 5/2008 |
| WO | 2009103165 | | 8/2009 |
| WO | 2010044607 | | 4/2010 |
| WO | 2011008560 | | 1/2011 |
| WO | 2011109671 | | 9/2011 |
| WO | 2012009283 | | 1/2012 |
| WO | WO2012088294 | * | 6/2012 |
| WO | 2012103380 | | 8/2012 |
| WO | WO2012103380 | * | 8/2012 |
| WO | WO2013039914 | * | 3/2013 |
| WO | WO2013068842 | * | 5/2013 |
| WO | 2014099864 | | 6/2014 |

OTHER PUBLICATIONS

Chen et al., "Versatile, Benzimidazole/Amine-Based Ambipolar Compounds for Electroluminescent Applications: Single-Layer, Blue, Fluorescent OLEOs, Hosts for Single-Layer, Phosphorescent OLEOs", Advanced Functional Materials, 2009, vol. 19, pp. 2661-2670.

Gustafsson et al. "Flexible Light-Emitting Diodes Made from Soluble Conducting Polymer," Nature, Jun. 11, 1992, vol. 357, pp. 477-479.

Kreimer-Birnbaum et al., "Modified Porphyrins, Chlorins, Phthalocyanines and Purpurins: Second-Generation Photosensitizers for Photodynamic Therapy", Semin Hematol, 1989, vol. 26, pp. 157-173.

Li et al., "Synthesis and Functional Properties of Strongly Luminescent Diphenylamine End-Capped Oligophenylenes", American Chemical Society, 2004, vol. 69, pp. 921-927.

International Search Report and Written Opinion in PCT Application No. PCT/US2012/022792, dated May 7, 2012.

Aratani, Sukekazu et al., "Collimated Light Source using Patterned Organic Light-Emitting Diodes and Microlens", Japanese Journal of Applied Physics, vol. 49, No. 4, pp. 42101-1 (2010).

Schwartz, Gregor et al., "Harvesting Triplet Excitons from Fluorescent Blue Emitters in White Organic Light-Emitting Diodes", Advanced Materials, vol. 19, No. 21, pp. 3672-3676 (2007).

International Search Report for PCT/US2013/075584 mailed on Dec. 17, 2013.

* cited by examiner

BIPOLAR HOSTS FOR LIGHT EMITTING DEVICES

CROSS REFERENCE TO RELATED APPLICATIONS

This application claims the benefit of U.S. Provisional Patent Application No. 61/735,478, filed Dec. 10, 2012, which is incorporated by reference herein in its entirety.

BACKGROUND

1. Field

This invention relates to compounds for use in organic light emitting diodes, such as for host materials.

2. Description of the Related Art

White organic light emitting devices (WOLEDs) have attracted much attention and been intensively studied due to their potential applications as backlight sources, full color displays, and general lighting. Among various device configurations to produce white light, a single-emissive-layer device employing phosphorescent materials in combination with proper host materials is desirable. Some advantages of such a device may include reduced overall cost, increased quantum efficiency, and easier fabrication. Since phosphorescent emitters can harvest both singlet and triplet excitons, use of phosphorescent emitters in WOLEDs may lead to the potential of achieving 100% internal quantum efficiency. Adding host materials may also reduce concentration quenching of the emissive materials and further increase the efficiency. In addition, adding host materials can reduce the required amount of expensive emissive material, and the fabrication of a single layer device is easier and more cost effective than a multiple layer device. As a result, the single-emissive-layer device with phosphorescent and host materials can lower the overall cost of fabricating the WOLEDs.

SUMMARY

Some embodiments include a compound represented by Formula 1:

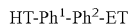

HT-Ph¹-Ph²-ET     (Formula 1)

wherein $Ph^1$ and $Ph^2$ are independently optionally substituted o-phenylene; HT is optionally substituted phenylcarbazolyl, optionally substituted (phenylcarbazolyl)phenyl, optionally substituted 4-(phenylnaphthylamino)phenyl, or optionally substituted 4-(diphenylamino)phenyl; and ET is optionally substituted benzimidazol-2-yl, optionally substituted benzimidazol-2-ylphenyl, optionally substituted di(benzimidazol-2-yl)phenyl, optionally substituted benzothiazol-2-yl, optionally substituted benzothiazol-2-ylphenyl, optionally substituted di(benzothiazol-2-yl)phenyl, optionally substituted benzoxazol-2-yl, optionally substituted benzoxazol-2-ylphenyl, optionally substituted di(benzoxazol-2-yl)phenyl, optionally substituted 3,3'-bipyridin-5-yl, optionally substituted quinolin-8-yl, optionally substituted quinolin-5-yl, or optionally substituted quinoxalin-5-yl.

Some embodiments provide a compound represented by Formula 2:

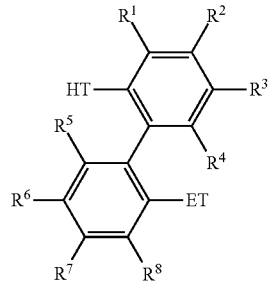

(Formula 2)

wherein $R^1$, $R^2$, $R^3$, $R^4$, $R^5$, $R^6$, $R^7$ and $R^8$, are independently H, $C_1$-$C_3$ alkyl, or $C_{1-3}$ perfluoroalkyl; HT is optionally substituted carbazoyl, optionally substituted phenylcarbazolyl, optionally substituted (phenylcarbazolyl)phenyl, optionally substituted phenylnaphthylamine, or optionally substituted diphenylamine; and ET is optionally substituted benzimidazol-2-yl, optionally substituted benzothiazol-2-yl, optionally substituted benzoxazol-2-yl, optionally substituted 3,3'-bipyridin-5-yl, optionally substituted quinolin-8-yl, optionally substituted quinolin-5-yl, and optionally substituted quinoxalin-5-yl.

Some embodiments also include optionally substituted N-phenyl-N-(4'''-(1-phenyl-1H-benzo[d]imidazol-2-yl)-[1,1':2',1'':2'',1'''-quaterphenyl]-4-yl)naphthalen-1-amine; optionally substituted 9-phenyl-3-(4''-(1-phenyl-1H-benzo[d]imidazol-2-yl)[1,1':2',1''-terphenyl]-2-yl)-9H-carbazole; optionally substituted 3-(3'',5''-bis(1-phenyl-1H-benzo[d]imidazol-2-yl)-[1,1':2',1''-terphenyl]-2-yl)-9-phenyl-9H-carbazole; optionally substituted 2,2'-(2''-(9-phenyl-9H-carbazol-3-yl)-[1,1':2',1''-terphenyl]-3,5-diyl)bis(benzo[d]oxazole); optionally substituted 3-(4''-(1-phenyl-1H-benzo[d]imidazol-2-yl)-[1,1':2',1''-terphenyl]-2-yl)-9-(p-tolyl)-9H-carbazole; or optionally substituted 9-phenyl-3-(4'''-(1-phenyl-1H-benzo[d]imidazol-2-yl)-[1,1':2',1'':2'',1'''-quaterphenyl]-4-yl)-9H-carbazole.

These compounds can be used in light-emitting devices, e.g. as host compounds.

Other embodiments provide an organic light-emitting diode device comprising a cathode; an anode; a light-emitting layer disposed between and electrically connected to the anode and the cathode; a hole-transport layer between the anode and the light-emitting layer; and an electron-transport layer between the cathode and the light-emitting layer; wherein at least one of the light-emitting layer, the hole-transport layer and the electron-transport layer comprise a host compound described herein.

Other embodiments provide an organic light-emitting diode device comprising: a cathode; an anode; and a light-emitting layer disposed between and electrically connected to the anode and the cathode; wherein the light-emitting layer comprises a host compound described herein.

These and other embodiments are described in greater detail below.

DETAILED DESCRIPTION

Figure 1:
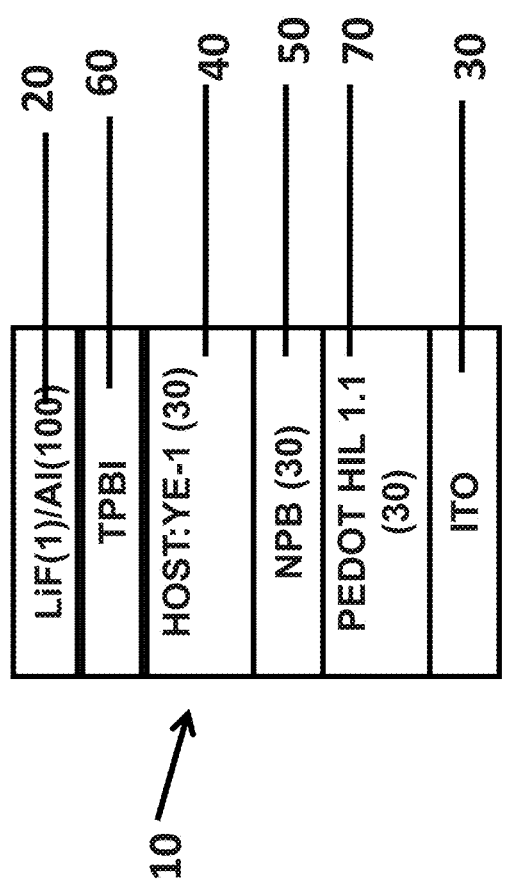
FIG. 1 is a schematic of a device incorporating an embodiment of a compound described herein.

The use of effective host materials can be helpful in making efficient WOLEDs. A host may be improved if it transports both holes and electrons efficiently at the same speed. A host may also be improved if its triplet energy is high enough to effectively confine the triplet excitons on the guest molecules. Some host materials are a mixture of hole-transport material and electron-transport material, which may pose potential problems such as phase separation, aggregation and lack of uniformity, and unequal material degradation rates. Thus, development of an ambipolar single molecule (i.e., a molecule capable of transporting both holes and electrons effectively) for a host material would be useful.

Some ambipolar single molecule hosts have been used in either single color or white OLED device applications. However, these molecules have either unbalanced hole-transport and electron-transport properties, or the devices made from these molecules have only moderate efficiency.

Thus, there is a need for a new type of ambipolar host that can be easily synthesized, possesses high thermal and electrochemical stability, and has well balanced hole-transport and electron-transport mobility when used as a host for phosphorescent emissive materials. Such a host may be used to achieve a simple device structure with high quantum efficiency and low turn-on voltage.

Unless otherwise indicated, when a compound or chemical structural feature such as aryl is referred to as being "optionally substituted," it includes a feature that has no substituents (i.e. unsubstituted), or a feature that is "substituted," meaning that the feature has one or more substituents. The term "substituent" has the broadest meaning known to one of ordinary skill in the art, and includes a moiety that replaces one or more hydrogen atoms in a parent compound or structural feature. The term "replaces" is merely used herein for convenience, and does not require that the compound be formed by replacing one atom with another. In some embodiments, a substituent may be an ordinary organic moiety known in the art, which may have a molecular weight (e.g. the sum of the atomic masses of the atoms of the substituent) of 15 g/mol to 50 g/mol, 15 g/mol to 100 g/mol, 15 g/mol to 150 g/mol, 15 g/mol to 200 g/mol, 15 g/mol to 300 g/mol, or 15 g/mol to 500 g/mol. In some embodiments, a substituent comprises, or consists of: 0-30, 0-20, 0-10, or 0-5 carbon atoms; and 0-30, 0-20, 0-10, or 0-5 heteroatoms, wherein each heteroatom may independently be: N, O, S, Si, F, Cl, Br, or I; provided that the substituent includes one C, N, O, S, Si, F, Cl, Br, or I atom.

Examples of substituents include, but are not limited to, hydrocarbyl, such as alkyl, alkenyl, alkynyl; heteroalkyl, including any alkyl wherein one or more heteroatoms replaces one or more carbon atoms, and some accompanying hydrogen atoms (e.g. N replaces CH, O replaces $CH_2$, Cl replaces $CH_3$, etc.), such as alkoxy, alkylthio, haloalkyl, haloalkoxy, amino, etc.; heteroalkenyl, including any alkenyl wherein one or more heteroatoms replaces one or more carbon atoms, and some accompanying hydrogen atoms, such as acyl, acyloxy, thiocarbonyl, alkylcarboxylate, O-carbamyl, N-carbamyl, O-thiocarbamyl, N-thiocarbamyl, C-amido, N-amido, sulfinyl, isocyanato, isothiocyanato, etc; heteroalkynyl, including any alkynyl wherein one or more heteroatoms replaces one or more carbon atoms, and some accompanying hydrogen atoms, such as cyano, thiocyanato, cyanato; aryl; heteroaryl; hydroxy; aryloxy; thiol; halo; S-sulfonamido; N-sulfonamido; nitro, silyl; sulfonyl; trihalomethanesulfonyl; trihalomethanesulfonamido; etc. In some embodiments, a substituent may be optionally substituted alkyl, —O-alkyl (e.g. —$OCH_3$, —$OC_2H5$, —$OC_3H_7$, —$OC_4H_9$, etc.), —S-alkyl (e.g. —$SCH_3$, —$SC_2H_5$, —$SC_3H_7$, —$SC_4H_9$, etc.), —NR'R", —OH, —SH, —CN, —$NO_2$, or a halogen, wherein R' and R" are independently H or optionally substituted alkyl.

For convenience, the term "molecular weight" is used with respect to a moiety or part of a molecule to indicate the sum of the atomic masses of the atoms in the moiety or part of a molecule, even though it may not be a complete molecule.

The term benzimidazol-2-yl refers to the ring system:

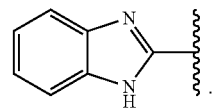

The term "benzimidazol-2-ylphenyl" refers to the ring system:

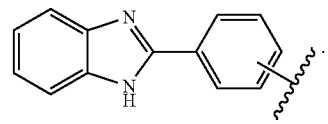

The term "di(benzimidazol-2-yl)phenyl" refers to the ring system:

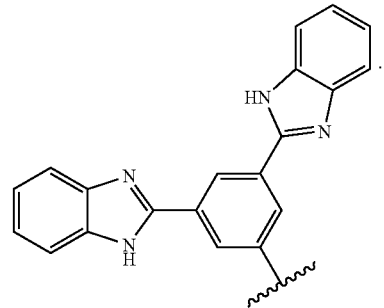 [SMILES: *c1cc(-c2nc3ccccc3[nH]2)cc(-c2nc3ccccc3[nH]2)c1]

In some, the benzimidazol-2-yl may have a substituent group $R^7$ as shown below:

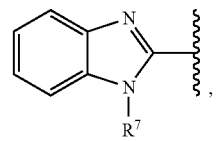

wherein $R^7$ is H, $C_1$-$C_3$ alkyl, or optionally substituted aryl, including, but not limited to phenyl and naphthyl. If $R^7$ is phenyl, the ring system can be referred to as 1-phenylbenzimidazol-2-yl.

The term benzoxazol-2-yl refers to the ring system:

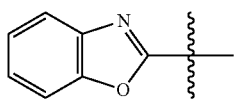 [SMILES: *c1nc2ccccc2o1]

The term "benzoxazol-2-ylphenyl" refers to the ring system:

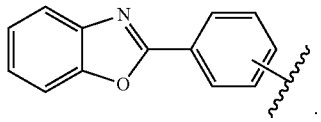

The term "di(benzoxazol-2-yl)phenyl" refers to the ring system:

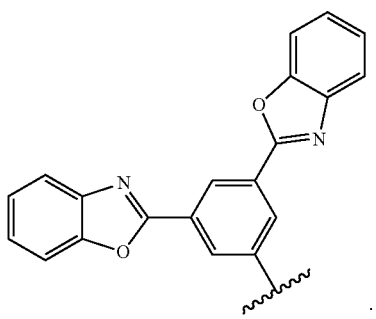 [SMILES: *c1cc(-c2nc3ccccc3o2)cc(-c2nc3ccccc3o2)c1]

The term benzothiazol-2-yl refers to the ring system:

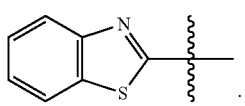 [SMILES: *c1nc2ccccc2s1]

The term "benzothiazol-2-ylphenyl" refers to the ring system:

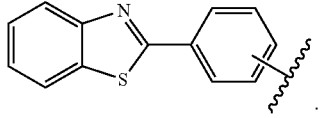

The term "quinolin-8-yl" refers to the ring system:

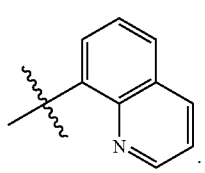 [SMILES: *c1cccc2cccnc12]

The term "quinolin-5-yl" refers to the ring system:

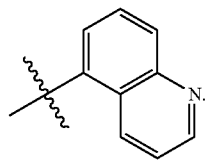 [SMILES: *c1cccc2ncccc12]

The term "quinoxalin-5-yl" refers to the ring system:

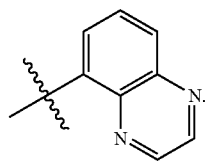 [SMILES: *c1cccc2nccnc12]

The term "carbazolyl" refers to the ring system:

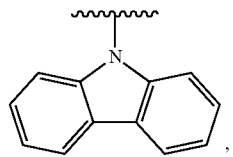 [SMILES: *n1c2ccccc2c2ccccc21]

which includes, but is not limited to

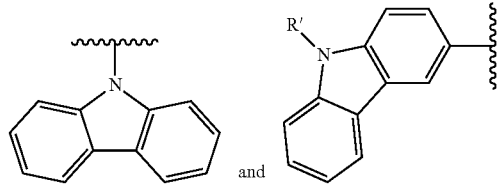

and wherein R' can be independently H, optionally substituted $C_1$-$C_3$ alkyl, or $C_{1-3}$ perfluoroalkyl.

The term "phenylcarbazolyl" refers to the ring systems:

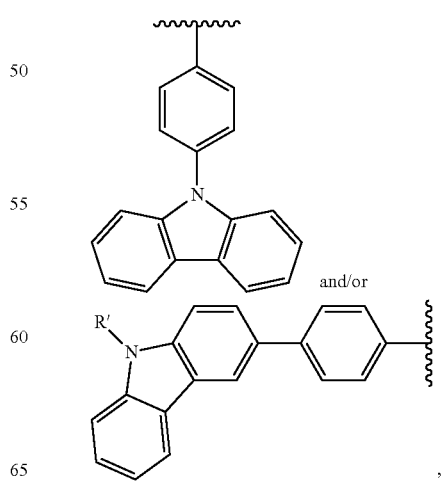

and/or wherein R' can be H, optionally substituted $C_1$-$C_3$ alkyl, or $C_{1-3}$ perfluoroalkyl.

The term "phenylcarbazolylphenyl" refers to the ring system:

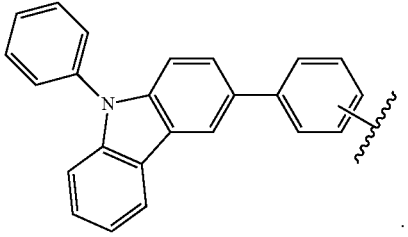

The term "4-(phenylcarbazolyl)phenyl" refers to the ring system:

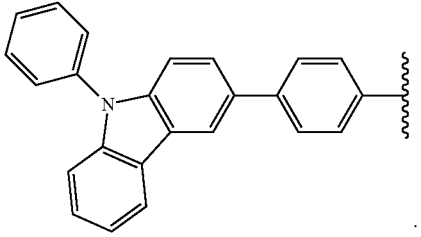 [SMILES: *c1ccc(-c2ccc3c(c2)c2ccccc2n3-c2ccccc2)cc1]

The term "diphenylamine" refers to the ring system:

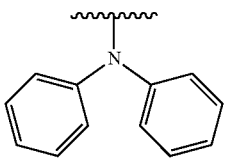

The term "phenylnaphthylamine" refers to the ring system:

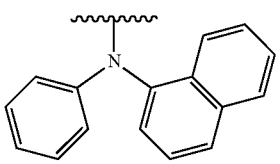

The term "4-(phenylnaphthylamino)phenyl" refers to the ring system

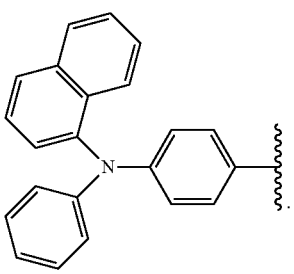 [SMILES: *c1ccc(N(c2ccccc2)c2cccc3ccccc23)cc1]

The term "4-(diphenylamino)phenyl" refers to the ring system:

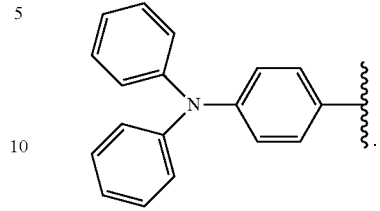

The term "o-phenylene" refers to:

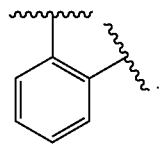

The term "1,3 interphenylene" refers to the ring system:

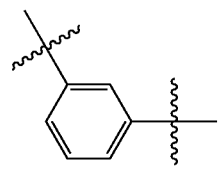 [SMILES: *c1cccc(*)c1]

The term "1,4 interphenylene" refers to the ring system:

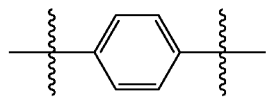

The term "perfluoroalkyl" refers to fluoroalkyl with a formula $C_nF_{2n+1}$ for a linear or branched structure, wherein n is any integer, such as 1, 2, 3, 4, 5, 6, 7, 8, 9, or 10, e.g., $CF_3$, $C_2F_5$, $C_3F_7$, $C_4F_9$, $C_5F_{11}$, $C_6F_{13}$, etc., or $C_nF_{2n}$ for a cyclic structure, e.g., cyclic $C_3F_6$, cyclic $C_4F_8$, cyclic $C_5F_{10}$, cyclic $C_6F_{12}$, etc. In other words, every hydrogen atom in alkyl is replaced by fluorine. For example, while not intending to be limiting, $C_{1-3}$ perfluoroalkyl refers to $CF_3$, $C_2F_5$, and $C_3F_7$ isomers. The term "perfluoroalkyl" refers to fluoroalkyl with a formula $C_nF_{2n+1}$ for a linear or branched structure, e.g., $CF_3$, $C_2F_5$, $C_3F_7$, $C_4F_9$, $C_5F_{11}$, $C_6F_{13}$, etc., or $C_nF_{2n}$ for a cyclic structure, e.g., cyclic $C_3F_6$, cyclic $C_4F_8$, cyclic $C_5F_{10}$, cyclic $C_6F_{12}$, etc. In other words, every hydrogen atom in alkyl is replaced by fluorine. For example, while not intending to be limiting, $C_{1-3}$ perfluoroalkyl refers to $CF_3$, $C_2F_5$, and $C_3F_7$ isomers.

With respect to Formula 1, $Ph^1$ is optionally substituted o-phenylene. If the o-phenylene is substituted, it may have 1, 2, 3, or 4 substituents. Any substituent can be included on the o-phenylene. In some embodiments, some or all of the substituents on the o-phenylene may have: from 0 to 15 carbon atoms and from 0 to 10 heteroatoms independently selected from: O, N, S, F, Cl, Br, and I; and/or a molecular weight of 15 g/mol to 500 g/mol. For example, the substituents may be $C_{1-10}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-10}$ alkoxy; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc. In some embodiments, any substituents of the o-phenylene are $C_{1-3}$ alkyl or $C_{1-3}$ perfluoroalkyl.

With respect to Formula 1, in some embodiments $Ph^1$ is:

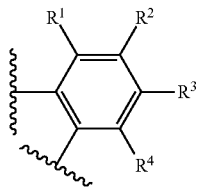

With respect to Formula 1, $Ph^2$ is optionally substituted o-phenylene. If the o-phenylene is substituted, it may have 1, 2, 3, or 4 substituents. Any substituent can be included on the o-phenylene. In some embodiments, some or all of the substituents on the o-phenylene may have: from 0 to 15 carbon atoms and from 0 to 10 heteroatoms independently selected from: O, N, S, F, Cl, Br, and I; and/or a molecular weight of 15 g/mol to 500 g/mol. For example, the substituents may be $C_{1-10}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-10}$ alkoxy; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc. In some embodiments, any substituents of the o-phenylene are $C_{1-3}$ alkyl or $C_{1-3}$ perfluoroalkyl.

With respect to Formula 1, in some embodiments, $Ph^2$ is:

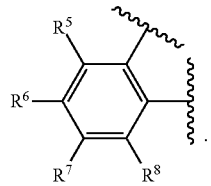

Some embodiments include a compound represented by Formula 2 or 3:

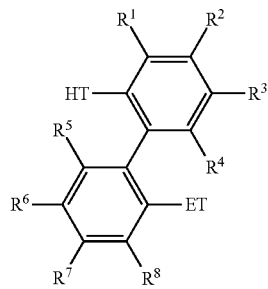

Formula 2

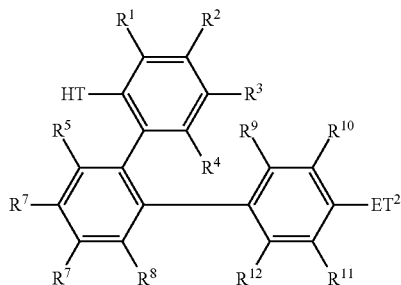

Formula 3

With respect to Formula 1, 2, or 3, HT is an optionally substituted phenylcarbazolyl, optionally substituted (phenylcarbazolyl)phenyl, optionally substituted 4-(phenylnaphthylamino)phenyl, or optionally substituted 4-(diphenylamino)phenyl. If HT is optionally substituted phenylcarbazolyl, it can have 0, 1, 2, 3, 4, 5, 6, 7, 8, 9, 10, 11, or 12 substituents. If HT is optionally substituted (phenylcarbazolyl)phenyl, it can have 0, 1, 2, 3, 4, 5, 6, 7, 8, 9, 10, 11, 12, 13, 14, 15, or 16 substituents. In some embodiments, HT is optionally substituted 4-(phenylcarbazolyl)phenyl. If HT is optionally substituted 4-(phenylnaphthylamino)phenyl, it can have 0, 1, 2, 3, 4, 5, 6, 7, 8, 9, 10, 11, 12, 13, 14, 15, or 16 substituents. If HT is optionally substituted 4-(diphenylamino)phenyl, it can have 0, 1, 2, 3, 4, 5, 6, 7, 8, 9, 10, 11, 12, 13, or 14 substituents. Any substituent can be included on HT. In some embodiments, some or all of the substituents on HT may have: from 0 to 15 carbon atoms and from 0 to 10 heteroatoms independently selected from: O, N, S, F, Cl, Br, and I; and/or a molecular weight of 15 g/mol to 500 g/mol. For example, the substituents may be $C_{1-10}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-10}$ alkoxy; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc. In some embodiments, HT has electron withdrawing substituents, including any group that can withdraw electron density from the parent ring system, such as $NO_2$, CN, $C_{1-6}$ acyl, $C_{1-6}$ alkylcarboxylate, $C_{1-6}$ fluoroalkyl, F, Cl, etc. In some embodiments, any substituents of HT are $C_{1-3}$ alkyl or $C_{1-3}$ perfluoroalkyl.

With respect to Formula 1, 2, or 3, in some embodiments HT is:

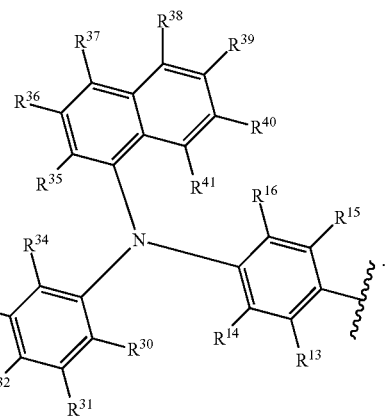

With respect to Formula 1, 2, or 3, in some embodiments HT is:

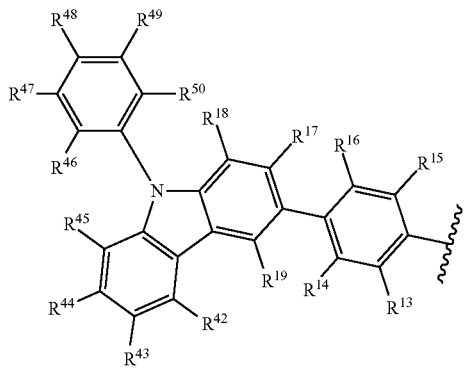

With respect to Formula 1, 2, or 3, in some embodiments HT is:

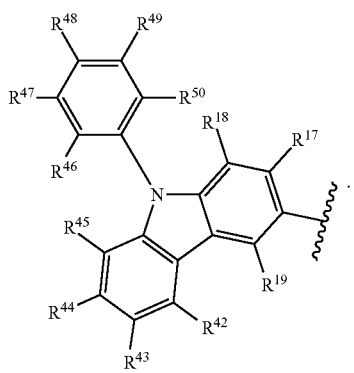

In another embodiment, HT can be:

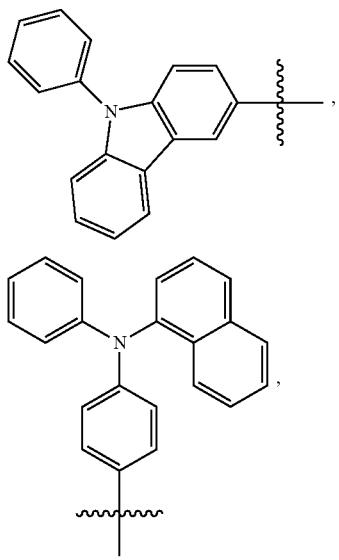

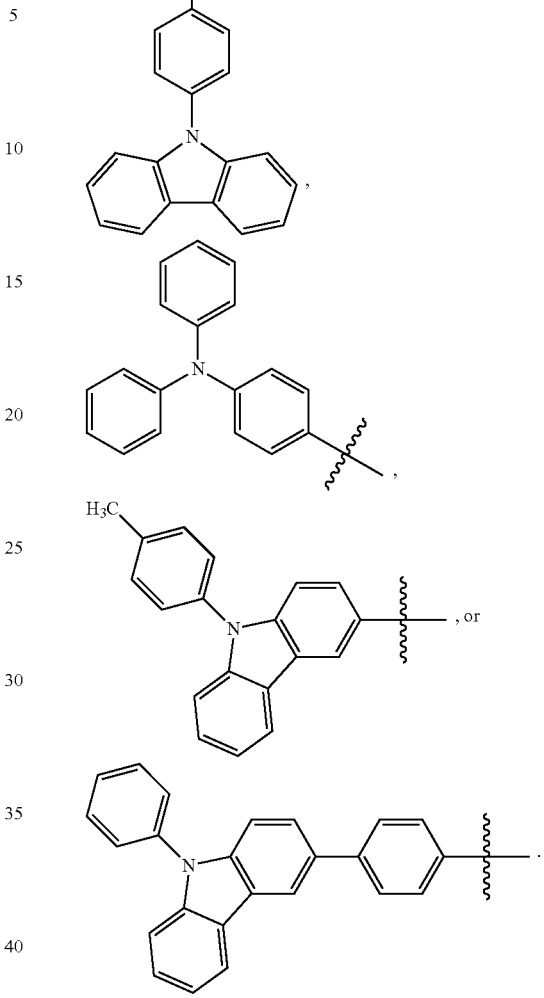

With respect to Formula 1 or 2, ET is optionally substituted benzimidazol-2-yl, optionally substituted benzimidazol-2-ylphenyl, optionally substituted di(benzimidazol-2-yl)phenyl, optionally substituted benzothiazol-2-ylphenyl, optionally substituted benzoxazol-2-ylphenyl, optionally substituted di(benzoxazol-2-yl)phenyl, optionally substituted 3,3'-bipyridin-5-yl, optionally substituted quinolin-8-yl, optionally substituted quinolin-5-yl, or optionally substituted quinoxalin-5-yl.

With respect to Formula 1 or 2, any substituent can be included on ET. In some embodiments, some or all of the substituents on ET may have: from 0 to 15 carbon atoms and from 0 to 10 heteroatoms independently selected from: O, N, S, F, Cl, Br, and I; and/or a molecular weight of 15 g/mol to 500 g/mol. For example, the substituents may be $C_{1-10}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-10}$ alkoxy; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc. In some embodiments, ET has electron donating substituents, including any group that can donate electron density to the parent ring system, such as $C_{1-6}$ alkyl, $C_{1-6}$ alkoxy, a $C_{1-6}$ amine, etc. In some embodiments, any substituents of ET are $C_{1-3}$ alkyl or $C_{1-3}$ perfluoroalkyl.

With respect to Formula 1 or 2, in some embodiments ET is:

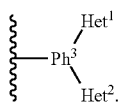

(Moiety A)

With respect to Formula 1 or 2, in some embodiments ET is:

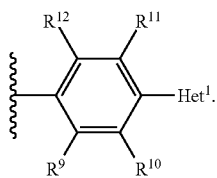

(Moiety B)

With respect to Formula 1 or 2, in some embodiments ET is:

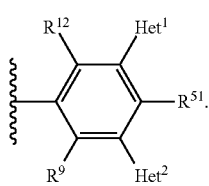

(Moiety C)

With respect to any relevant structural representation, such as Moiety A, Moiety B, or Moiety C, $Ph^3$ is phenylene, $Het^1$ is optionally substituted 1-phenylbenzimidazol-2-yl or optionally substituted benzoxazol-2-yl; and $Het^2$ is H, is optionally substituted 1-phenylbenzimidazol-2-yl, or optionally substituted benzoxazol-2-yl.

If $Het^1$ is optionally substituted 1-phenylbenzimidazol-2-yl, it can have 0, 1, 2, 3, 4, 5, 6, 7, 8, or 9 substituents. If $Het^1$ is optionally substituted benzoxazol-2-yl, it can have 0, 1, 2, 3, or 4 substituents.

In some embodiments, $Het^1$ is

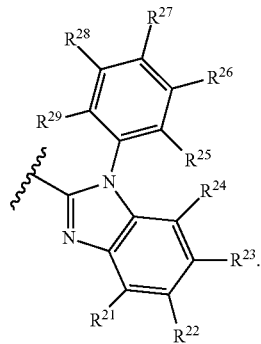

In some embodiments, $Het^1$ is

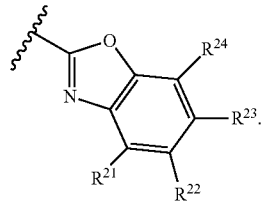

In some embodiments, $Het^1$ is

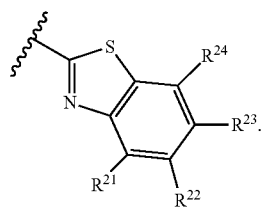

If $Het^2$ is optionally substituted 1-phenylbenzimidazol-2-yl, it can have 0, 1, 2, 3, 4, 5, 6, 7, 8, or 9 substituents. If $Het^2$ is optionally substituted benzoxazol-2-yl, it can have 0, 1, 2, 3, or 4 substituents.

In some embodiments, $Het^2$ is H.
In some embodiments, $Het^2$ is

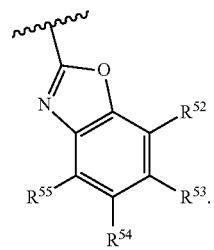

In some embodiments, $Het^2$ is

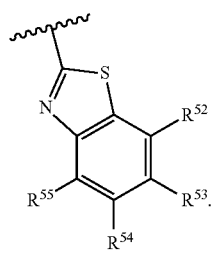

In some embodiments, $Het^2$ is

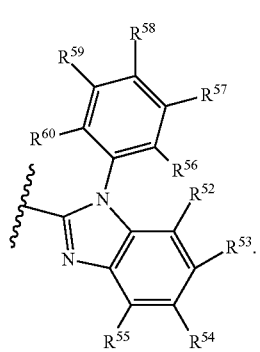

With respect to Formula 1 or 2, in some embodiments ET is:
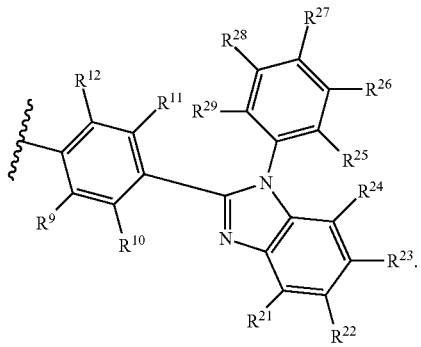
With respect to Formula 1 or 2, in some embodiments ET is:
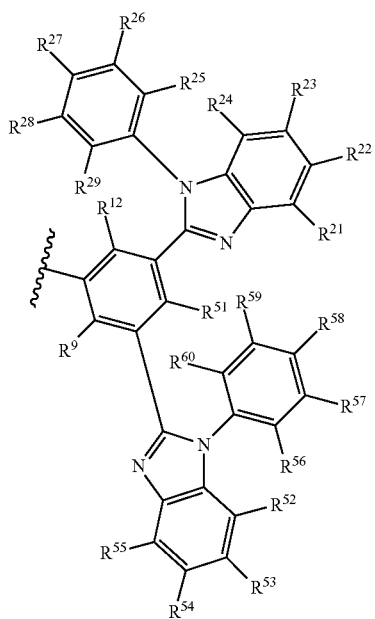
With respect to Formula 1 or 2, in some embodiments ET is:
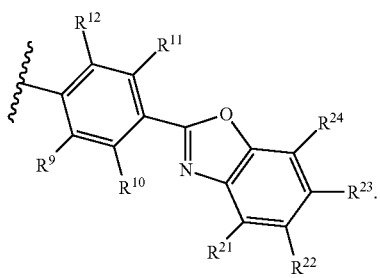
With respect to Formula 1 or 2, in some embodiments ET is:
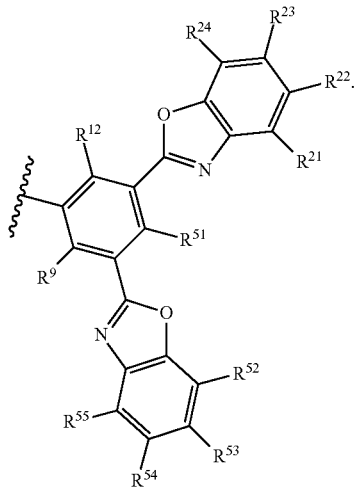
With respect to Formula 1 or 2, in some embodiments ET is:
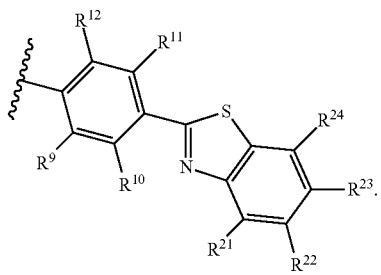
In another embodiment, ET can be:
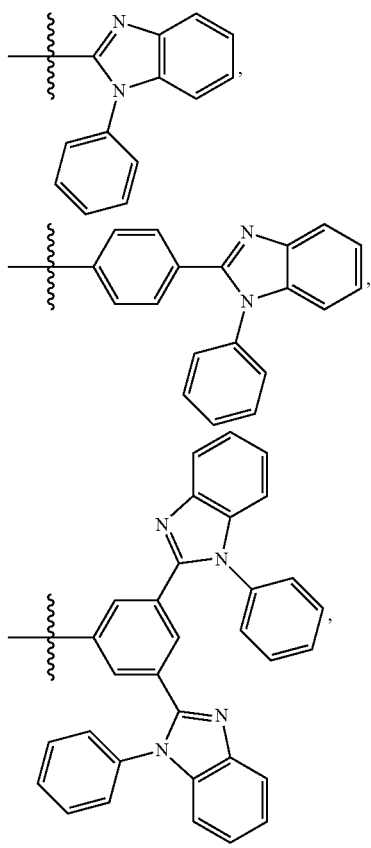

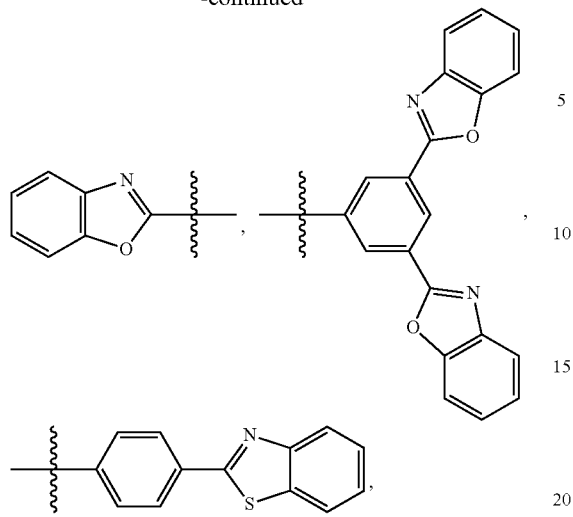
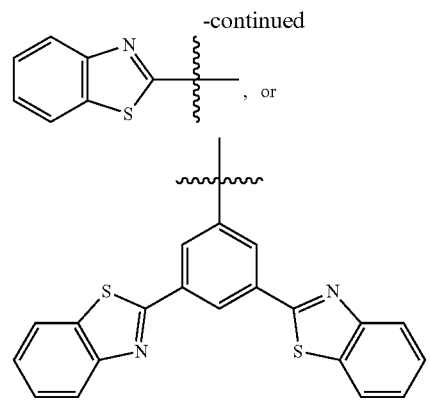
With respect to Formula 3, ET² is an optionally substituted benzimidazol-2-yl.
Formula 4
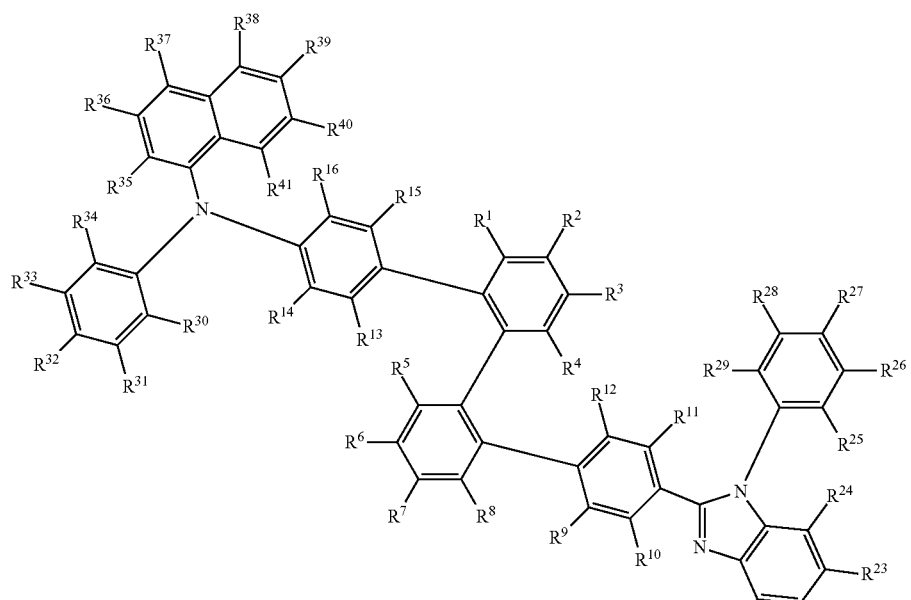
Formula 5
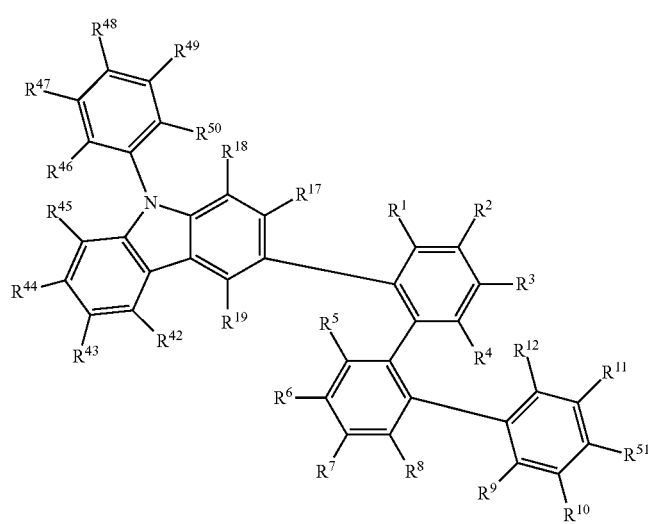

Forumla 6
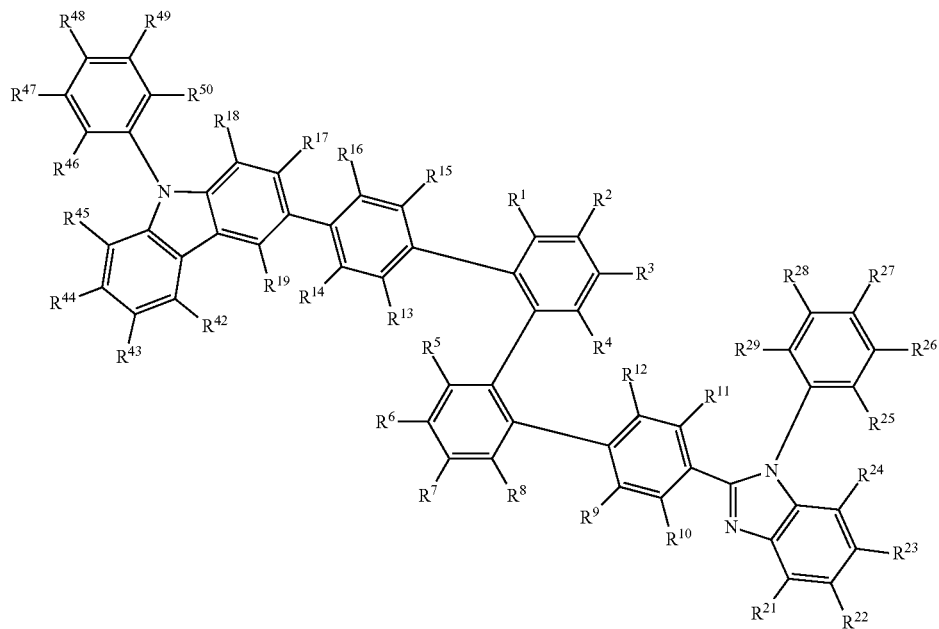
Formula 7
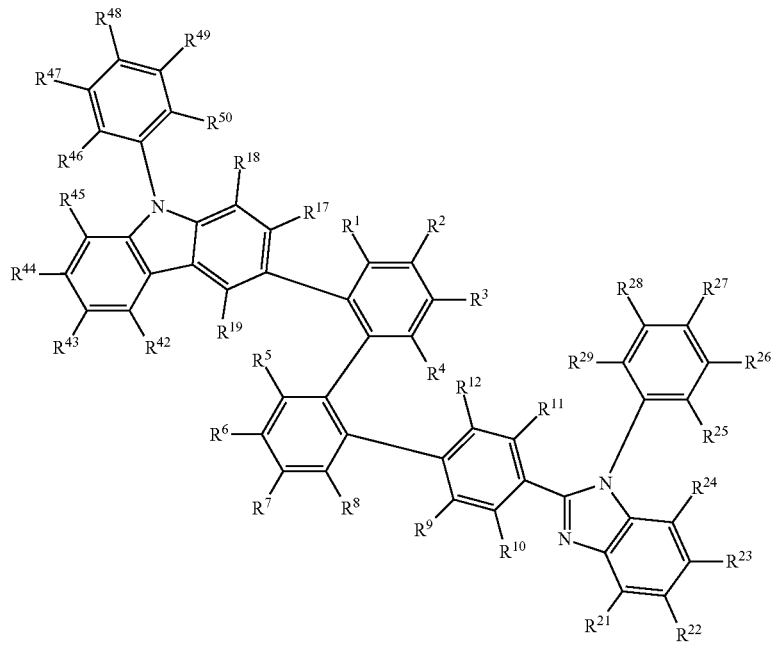

Formula 8

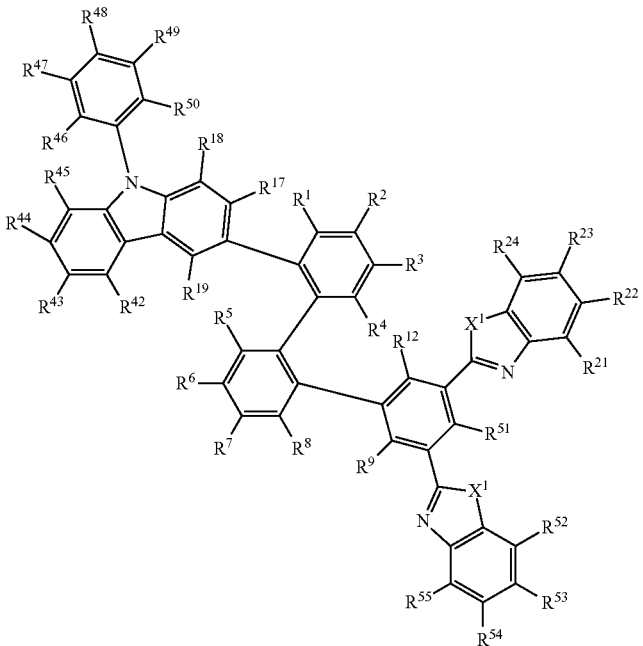

Formula 9

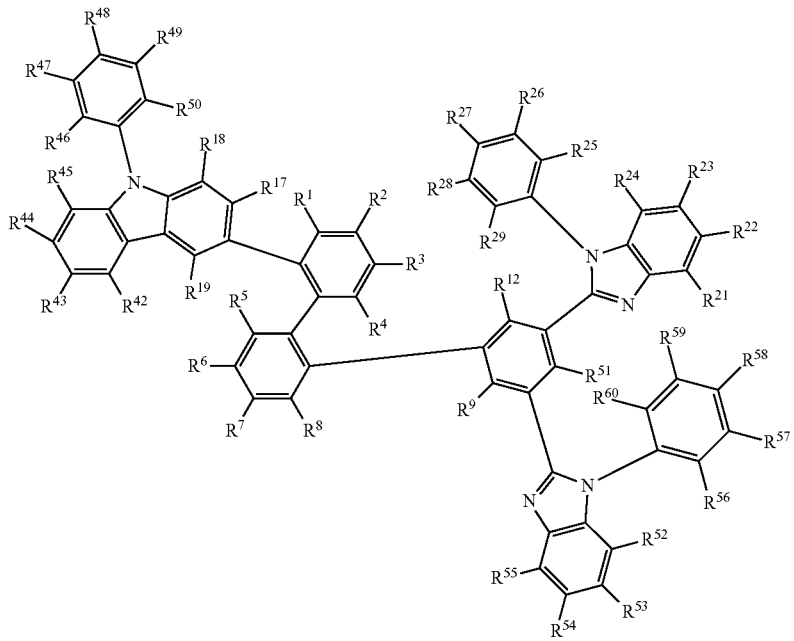

With respect to any relevant structural representations, such as Formulas 2, 3, 4, 5, 6, 7, 8, or 9, $R^{1-60}$ may be H or any substituent, such as a substituent having from 0 to 6 carbon atoms and from 0 to 5 heteroatoms, wherein each heteroatom is independently: O, N, S, F, Cl, Br, or I, and/or having a molecular weight of 15 g/mol to 300 g/mol. Any of $R^1$-$R^{60}$ may comprise: a) 1 or more alkyl moieties optionally substituted with, or optionally connected by or to, b) 1 or more functional groups, such as C=C, C≡C, CO, $CO_2$, CON, $NCO_2$, OH, SH, O, S, N, N=C, F, Cl, Br, I, CN, $NO_2$, $CO_2H$, $NH_2$, etc.; or may be a substituent having no alkyl portion, such as F, Cl, Br, I, $NO_2$, CN, $NH_2$, OH, COH, $CO_2H$, etc.

With respect to any relevant structural representations, such as Formulas 2, 3, 4, 5, 6, 7, 8, or 9, some non-limiting examples of $R^{1-60}$ may independently include $R^A$, F, Cl, CN, $OR^A$, $CF_3$, $NO_2$, $NR^AR^B$, $COR^A$, $CO_2R^A$, $OCOR_A$, $NR^ACOR^B$, $CONR^AR^B$, etc. In some embodiments, $R^{1-60}$ may be may be H; F; Cl; CN; $CF_3$; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; $C_{1-6}$ amino, such as —$NHCH_3$, —$NH(CH_3)_2$, —$NHCH_2CH_3$, etc.; $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.; CHO; $C_{2-6}$—CO-alkyl, such as —$COCH_3$, —COC$_2$H$_5$, —COC$_3$H$_7$, COC$_4$H$_9$, —COC$_5$H$_{11}$, etc.; CO$_2$H; C$_{2-6}$—CO$_2$-alkyl, —CO$_2$CH$_3$, —CO$_2$C$_2$H$_5$, —CO$_2$C$_3$H$_7$, CO$_2$C$_4$H$_9$, —COC$_5$H$_{11}$, etc. In some embodiments, R$^{1-60}$ may independently be H, C$_1$-C$_3$ alkyl, or C$_{1-3}$ perfluoroalkyl. In some embodiments, R$^{1-60}$ may be H.

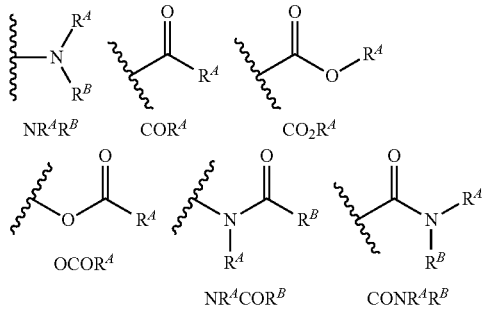

Each R$^A$ may independently be H, or C$_{1-12}$ alkyl, including: linear or branched alkyl having a formula C$_a$H$_{a+1}$, or cycloalkyl having a formula C$_a$H$_{a-1}$, wherein a is 1, 2, 3, 4, 5, 6, 7, 8, 9, 10, 11, or 12, such as linear or branched alkyl of a formula: CH$_3$, C$_2$H$_5$, C$_3$H$_7$, C$_4$H$_9$, C$_5$H$_{11}$, C$_6$H$_{13}$, C$_7$H$_{15}$, C$_8$H$_{17}$, C$_9$H$_{19}$, C$_{10}$H$_{21}$, etc., or cycloalkyl of a formula: C$_3$H$_5$, C$_4$H$_7$, C$_5$H$_9$, C$_6$H$_{11}$, C$_7$H$_{13}$, C$_8$H$_{15}$, C$_9$H$_{17}$, C$_{10}$H$_{19}$, etc. In some embodiments, R$^A$ may be H or C$_{1-6}$ alkyl. In some embodiments, R$^A$ may be H or C$_{1-3}$ alkyl. In some embodiments, R$^A$ may be H or CH$_3$. In some embodiments, R$^A$ may be H.

Each R$^B$ may independently be H, or C$_{1-12}$ alkyl, including: linear or branched alkyl having a formula C$_a$H$_{a+1}$, or cycloalkyl having a formula C$_a$H$_a$, wherein a is 1, 2, 3, 4, 5, 6, 7, 8, 9, 10, 11, or 12, such as linear or branched alkyl of a formula: CH$_3$, C$_2$H$_5$, C$_3$H$_7$, C$_4$H$_9$, C$_5$H$_{11}$, C$_6$H$_{13}$, C$_8$H$_{17}$, C$_7$H$_{15}$, C$_9$H$_{19}$, C$_{10}$H$_{21}$, etc., or cycloalkyl of a formula: C$_3$H$_5$, C$_4$H$_7$, C$_5$H$_9$, C$_6$H$_{11}$, C$_7$H$_{13}$, C$_8$H$_{15}$, C$_9$H$_{17}$, C$_{10}$H$_{19}$, etc. In some embodiments, R$^B$ may be H or C$_{1-3}$ alkyl. In some embodiments, R$^B$ may be H or CH$_3$. In some embodiments, R$^B$ may be H.

With respect to any relevant structural representation, such as Formulas 2, 3, 4, 5, 6, 7, 8, or 9, in some embodiments R$^1$ is H, C$_1$-C$_3$ alkyl, or C$_{1-3}$ perfluoroalkyl. In some embodiments, R$^1$ is H. Additionally, for any embodiments recited in this paragraph, all remaining relevant groups of R$^{1-60}$ may independently be R$^A$, F, Cl, CN, OR$^A$, CF$_3$, NO$_2$, NR$^A$R$^B$, COR$^A$, CO$_2$R$^A$, OCORA, NR$^A$COR$^B$, CONR$^A$R$^B$; may independently be H; F; Cl; CN; CF$_3$; OH; NH$_2$; C$_{1-6}$ alkyl; C$_{1-6}$ amino; C$_{1-6}$ alkoxy; CHO; C$_{2-6}$—CO-alkyl; CO$_2$H; or C$_{2-6}$—CO$_2$-alkyl; may independently be H, C$_1$-C$_3$ alkyl, or C$_{1-3}$ perfluoroalkyl; or may be H.

With respect to any relevant structural representation, such as Formulas 2, 3, 4, 5, 6, 7, 8, or 9, in some embodiments R$^2$ is H, C$_1$-C$_3$ alkyl, or C$_{1-3}$ perfluoroalkyl. In some embodiments, R$^2$ is H. Additionally, for any embodiments recited in this paragraph, all remaining relevant groups of R$^{1-60}$ may independently be R$^A$, F, Cl, CN, OR$^A$, CF$_3$, NO$_2$, NR$^A$R$^B$, COR$^A$, CO$_2$R$^A$, OCORA, NR$^A$COR$^B$, CONR$^A$R$^B$; may independently be H; F; Cl; CN; CF$_3$; OH; NH$_2$; C$_{1-6}$ alkyl; C$_{1-6}$ amino; C$_{1-6}$ alkoxy; CHO; C$_{2-6}$—CO-alkyl; CO$_2$H; or C$_{2-6}$—CO$_2$-alkyl; may independently be H, C$_1$-C$_3$ alkyl, or C$_{1-3}$ perfluoroalkyl; or may be H.

With respect to any relevant structural representation, such as Formulas 2, 3, 4, 5, 6, 7, 8, or 9, in some embodiments R$^3$ is H, C$_1$-C$_3$ alkyl, or C$_{1-3}$ perfluoroalkyl. In some embodiments, R$^3$ is H. Additionally, for any embodiments recited in this paragraph, all remaining relevant groups of R$^{1-60}$ may independently be R$^A$, F, Cl, CN, OR$^A$, CF$_3$, NO$_2$, NR$^A$R$^B$, COR$^A$, CO$_2$R$^A$, OCORA, NR$^A$COR$^B$, CONR$^A$R$^B$; may independently be H; F; Cl; CN; CF$_3$; OH; NH$_2$; C$_{1-6}$ alkyl; C$_{1-6}$ amino; C$_{1-6}$ alkoxy; CHO; C$_{2-6}$—CO-alkyl; CO$_2$H; or C$_{2-6}$—CO$_2$-alkyl; may independently be H, C$_1$-C$_3$ alkyl, or C$_{1-3}$ perfluoroalkyl; or may be H.

With respect to any relevant structural representation, such as Formulas 2, 3, 4, 5, 6, 7, 8, or 9, in some embodiments R$^4$ is H, C$_1$-C$_3$ alkyl, or C$_{1-3}$ perfluoroalkyl. In some embodiments, R$^4$ is H. Additionally, for any embodiments recited in this paragraph, all remaining relevant groups of R$^{1-60}$ may independently be R$^A$, F, Cl, CN, OR$^A$, CF$_3$, NO$_2$, NR$^A$R$^B$, COR$^A$, CO$_2$R$^A$, OCORA, NR$^A$COR$^B$, CONR$^A$R$^B$; may independently be H; F; Cl; CN; CF$_3$; OH; NH$_2$; C$_{1-6}$ alkyl; C$_{1-6}$ amino; C$_{1-6}$ alkoxy; CHO; C$_{2-6}$—CO-alkyl; CO$_2$H; or C$_{2-6}$—CO$_2$-alkyl; may independently be H, C$_1$-C$_3$ alkyl, or C$_{1-3}$ perfluoroalkyl; or may be H.

With respect to any relevant structural representation, such as Formulas 2, 3, 4, 5, 6, 7, 8, or 9, in some embodiments R$^5$ is H, C$_1$-C$_3$ alkyl, or C$_{1-3}$ perfluoroalkyl. In some embodiments, R$^5$ is H. Additionally, for any embodiments recited in this paragraph, all remaining relevant groups of R$^{1-60}$ may independently be R$^A$, F, Cl, CN, OR$^A$, CF$_3$, NO$_2$, NR$^A$R$^B$, COR$^A$, CO$_2$R$^A$, OCORA, NR$^A$COR$^B$, CONR$^A$R$^B$; may independently be H; F; Cl; CN; CF$_3$; OH; NH$_2$; C$_{1-6}$ alkyl; C$_{1-6}$ amino; C$_{1-6}$ alkoxy; CHO; C$_{2-6}$—CO-alkyl; CO$_2$H; or C$_{2-6}$—CO$_2$-alkyl; may independently be H, C$_1$-C$_3$ alkyl, or C$_{1-3}$ perfluoroalkyl; or may be H.

With respect to any relevant structural representation, such as Formulas 2, 3, 4, 5, 6, 7, 8, or 9, in some embodiments R$^6$ is H, C$_1$-C$_3$ alkyl, or C$_{1-3}$ perfluoroalkyl. In some embodiments, R$^6$ is H. Additionally, for any embodiments recited in this paragraph, all remaining relevant groups of R$^{1-60}$ may independently be R$^A$, F, Cl, CN, OR$^A$, CF$_3$, NO$_2$, NR$^A$R$^B$, COR$^A$, CO$_2$R$^A$, OCORA, NR$^A$COR$^B$, CONR$^A$R$^B$; may independently be H; F; Cl; CN; CF$_3$; OH; NH$_2$; C$_{1-6}$ alkyl; C$_{1-6}$ amino; C$_{1-6}$ alkoxy; CHO; C$_{2-6}$—CO-alkyl; CO$_2$H; or C$_{2-6}$—CO$_2$-alkyl; may independently be H, C$_1$-C$_3$ alkyl, or C$_{1-3}$ perfluoroalkyl; or may be H.

With respect to any relevant structural representation, such as Formulas 2, 3, 4, 5, 6, 7, 8, or 9, in some embodiments R$^7$ is H, C$_1$-C$_3$ alkyl, or C$_{1-3}$ perfluoroalkyl. In some embodiments, R$^7$ is H. Additionally, for any embodiments recited in this paragraph, all remaining relevant groups of R$^{1-60}$ may independently be R$^A$, F, Cl, CN, OR$^A$, CF$_3$, NO$_2$, NR$^A$R$^B$, COR$^A$, CO$_2$R$^A$, OCORA, NR$^A$COR$^B$, CONR$^A$R$^B$; may independently be H; F; Cl; CN; CF$_3$; OH; NH$_2$; C$_{1-6}$ alkyl; C$_{1-6}$ amino; C$_{1-6}$ alkoxy; CHO; C$_{2-6}$—CO-alkyl; CO$_2$H; or C$_{2-6}$—CO$_2$-alkyl; may independently be H, C$_1$-C$_3$ alkyl, or C$_{1-3}$ perfluoroalkyl; or may be H.

With respect to any relevant structural representation, such as Formulas 2, 3, 4, 5, 6, 7, 8, or 9, in some embodiments R$^8$ is H, C$_1$-C$_3$ alkyl, or C$_{1-3}$ perfluoroalkyl. In some embodiments, R$^8$ is H. Additionally, for any embodiments recited in this paragraph, all remaining relevant groups of R$^{1-60}$ may independently be R$^A$, F, Cl, CN, OR$^A$, CF$_3$, NO$_2$, NR$^A$R$^B$, COR$^A$, CO$_2$R$^A$, OCORA, NR$^A$COR$^B$, CONR$^A$R$^B$; may independently be H; F; Cl; CN; CF$_3$; OH; NH$_2$; C$_{1-6}$ alkyl; C$_{1-6}$ amino; C$_{1-6}$ alkoxy; CHO; C$_{2-6}$—CO-alkyl; CO$_2$H; or C$_{2-6}$—CO$_2$-alkyl; may independently be H, C$_1$-C$_3$ alkyl, or C$_{1-3}$ perfluoroalkyl; or may be H.

With respect to any relevant structural representation, such as Formulas 2, 3, 4, 5, 6, 7, 8, or 9, in some embodiments, R$^1$, R$^2$, R$^3$, R$^4$, R$^5$, R$^6$, R$^7$ and R$^8$ are H.

With respect to any relevant structural representation, such as Formulas 3, 4, 5, 6, 7, 8, or 9, in some embodiments R$^9$ is H, $C_1$-$C_3$ alkyl, or $C_{1-3}$ perfluoroalkyl. In some embodiments, $R^9$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 3, 4, 5, 6, or 7, in some embodiments $R^{10}$ is H, $C_1$-$C_3$ alkyl, or $C_{1-3}$ perfluoroalkyl. In some embodiments, $R^{10}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 3, 4, 5, 6, or 7, in some embodiments $R^{11}$ is H, $C_1$-$C_3$ alkyl, or $C_{1-3}$ perfluoroalkyl. In some embodiments, $R^{11}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 3, 4, 5, 6, 7, 8, or 9, in some embodiments $R^{12}$ is H, $C_1$-$C_3$ alkyl, or $C_{1-3}$ perfluoroalkyl. In some embodiments, $R^{12}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 3, 4, 5, 6, 7, 8, or 9, in some embodiments $R^1$, $R^2$, $R^3$, $R^4$, $R^5$, $R^6$, $R^7$, $R^8$, $R^9$, $R^{19}$, $R^{11}$ and $R^{12}$ are independently H, $C_1$-$C_3$ alkyl, or $C_{1-3}$ perfluoroalkyl. In some embodiments, $R^1$, $R^2$, $R^3$, $R^4$, $R^5$, $R^6$, $R^7$, $R^8$, $R^9$, $R^{19}$, $R^{11}$ and $R^{12}$ are H.

With respect to any relevant structural representation, such as Formulas 4 or 6, in some embodiments $R^{13}$ is H, $C_1$-$C_3$ alkyl, or $C_{1-3}$ perfluoroalkyl. In some embodiments, $R^{13}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 4 or 6, in some embodiments $R^{14}$ is H, $C_1$-$C_3$ alkyl, or $C_{1-3}$ perfluoroalkyl. In some embodiments, $R^{14}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 4 or 6, in some embodiments $R^{15}$ is H, $C_1$-$C_3$ alkyl, or $C_{1-3}$ perfluoroalkyl. In some embodiments, $R^{15}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 4 or 6, in some embodiments $R^{16}$ is H, $C_1$-$C_3$ alkyl, or $C_{1-3}$ perfluoroalkyl. In some embodiments, $R^{16}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 5, 6, 7, 8, or 9, in some embodiments $R^{17}$ is H, $C_1$-$C_3$ alkyl, or $C_{1-3}$ perfluoroalkyl. In some embodiments, $R^{17}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 5, 6, 7, 8, or 9, in some embodiments $R^{18}$ is H, $C_1$-$C_3$ alkyl, or $C_{1-3}$ perfluoroalkyl. In some embodiments, $R^{18}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 5, 6, 7, 8, or 9, in some embodiments $R^{19}$ is H, $C_1$-$C_3$ alkyl, or $C_{1-3}$ perfluoroalkyl. In some embodiments, $R^{19}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 4, 6, 7, 8, or 9, in some embodiments $R^{21}$ is H, $C_1$-$C_3$ alkyl, or $C_{1-3}$ perfluoroalkyl. In some embodiments, $R^{21}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 4, 6, 7, 8, or 9, in some embodiments $R^{22}$ is H, $C_1$-$C_3$ alkyl, or $C_{1-3}$ perfluoroalkyl. In some embodiments, $R^{22}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, OCORA, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 4, 6, 7, 8, or 9, in some embodiments $R^{23}$ is H, $C_1$-$C_3$ alkyl, or $C_{1-3}$ perfluoroalkyl. In some embodiments, $R^{23}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, OCORA, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 4, 6, 7, 8, or 9, in some embodiments $R^{24}$ is H, $C_1$-$C_3$ alkyl, or $C_{1-3}$ perfluoroalkyl. In some embodiments, $R^{24}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, OCORA, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 4, 6, 7, or 9, in some embodiments $R^{25}$ is H, $C_1$-$C_3$ alkyl, or $C_{1-3}$ perfluoroalkyl. In some embodiments, $R^{25}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, OCORA, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 4, 6, 7, or 9, in some embodiments $R^{26}$ is H, $C_1$-$C_3$ alkyl, or $C_{1-3}$ perfluoroalkyl. In some embodiments, $R^{26}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, OCORA, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 4, 6, 7, or 9, in some embodiments $R^{27}$ is H, $C_1$-$C_3$ alkyl, or $C_{1-3}$ perfluoroalkyl. In some embodiments, $R^{27}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, OCORA, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 4, 6, 7, or 9, in some embodiments $R^{28}$ is H, $C_1$-$C_3$ alkyl, or $C_{1-3}$ perfluoroalkyl. In some embodiments, $R^{28}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, OCORA, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 4, 6, 7, or 9, in some embodiments $R^{29}$ is H, $C_1$-$C_3$ alkyl, or $C_{1-3}$ perfluoroalkyl. In some embodiments, $R^{29}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, OCORA, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formula 4, in some embodiments $R^{30}$ is H, $C_1$-$C_3$ alkyl, or $C_{1-3}$ perfluoroalkyl. In some embodiments, $R^{30}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, OCORA, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formula 4, in some embodiments $R^{31}$ is H, $C_1$-$C_3$ alkyl, or $C_{1-3}$ perfluoroalkyl. In some embodiments, $R^{31}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, OCORA, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formula 4, in some embodiments $R^{32}$ is H, $C_1$-$C_3$ alkyl, or $C_{1-3}$ perfluoroalkyl. In some embodiments, $R^{32}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, OCORA, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formula 4, in some embodiments $R^{33}$ is H, $C_1$-$C_3$ alkyl, or $C_{1-3}$ perfluoroalkyl. In some embodiments, $R^{33}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, OCORA, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formula 4, in some embodiments $R^{34}$ is H, $C_1$-$C_3$ alkyl, or $C_{1-3}$ perfluoroalkyl. In some embodiments, $R^{34}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formula 4, in some embodiments $R^{35}$ is H, $C_1$-$C_3$ alkyl, or $C_{1-3}$ perfluoroalkyl. In some embodiments, $R^{35}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formula 4, in some embodiments $R^{36}$ is H, $C_1$-$C_3$ alkyl, or $C_{1-3}$ perfluoroalkyl. In some embodiments, $R^{36}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formula 4, in some embodiments $R^{37}$ is H, $C_1$-$C_3$ alkyl, or $C_{1-3}$ perfluoroalkyl. In some embodiments, $R^{37}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formula 4, in some embodiments $R^{38}$ is H, $C_1$-$C_3$ alkyl, or $C_{1-3}$ perfluoroalkyl. In some embodiments, $R^{38}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formula 4, in some embodiments $R^{39}$ is H, $C_1$-$C_3$ alkyl, or $C_{1-3}$ perfluoroalkyl. In some embodiments, $R^{39}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formula 4, in some embodiments $R^{40}$ is H, $C_1$-$C_3$ alkyl, or $C_{1-3}$ perfluoroalkyl. In some embodiments, $R^{40}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formula 4, in some embodiments $R^{41}$ is H, $C_1$-$C_3$ alkyl, or $C_{1-3}$ perfluoroalkyl. In some embodiments, $R^{41}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 5, 6, 7, 8, or 9, in some embodiments $R^{42}$ is H, $C_1$-$C_3$ alkyl, or $C_{1-3}$ perfluoroalkyl. In some embodiments, $R^{42}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 5, 6, 7, 8, or 9, in some embodiments $R^{43}$ is H, $C_1$-$C_3$ alkyl, or $C_{1-3}$ perfluoroalkyl. In some embodiments, $R^{43}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 5, 6, 7, 8, or 9, in some embodiments $R^{44}$ is H, $C_1$-$C_3$ alkyl, or $C_{1-3}$ perfluoroalkyl. In some embodiments, $R^{44}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 5, 6, 7, 8, or 9, in some embodiments $R^{45}$ is H, $C_1$-$C_3$ alkyl, or $C_{1-3}$ perfluoroalkyl. In some embodiments, $R^{45}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 5, 6, 7, 8, or 9, in some embodiments $R^{46}$ is H, $C_1$-$C_3$ alkyl, or $C_{1-3}$ perfluoroalkyl. In some embodiments, $R^{46}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 5, 6, 7, 8, or 9, in some embodiments $R^{47}$ is H, $C_1$-$C_3$ alkyl, or $C_{1-3}$ perfluoroalkyl. In some embodiments, $R^{47}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^A R^B$, $COR^A$, $CO_2 R^A$, OCORA, $NR^A COR^B$, $CONR^A R^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 5, 6, 7, 8, or 9, in some embodiments $R^{48}$ is H, $C_1$-$C_3$ alkyl, or $C_{1-3}$ perfluoroalkyl. In some embodiments, $R^{48}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^A R^B$, $COR^A$, $CO_2 R^A$, OCORA, $NR^A COR^B$, $CONR^A R^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 5, 6, 7, 8, or 9, in some embodiments $R^{49}$ is H, $C_1$-$C_3$ alkyl, or $C_{1-3}$ perfluoroalkyl. In some embodiments, $R^{49}$ is H. In some embodiments, $R^{49}$ is methyl. Additionally, for any embodiments recited in this paragraph, all remaining relevant groups of $R^{1-60}$ may independently be $R^A$, F, Cl, CN, $OR^A$, $CF_3$, $NO_2$, $NR^A R^B$, $COR^A$, $CO_2 R^A$, OCORA, $NR^A COR^B$, $CONR^A R^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 5, 6, 7, 8, or 9, in some embodiments $R^{50}$ is H, $C_1$-$C_3$ alkyl, or $C_{1-3}$ perfluoroalkyl. In some embodiments, $R^{50}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^A R^B$, $COR^A$, $CO_2 R^A$, OCORA, $NR^A COR^B$, $CONR^A R^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 8, or 9, in some embodiments $R^{51}$ is H, $C_1$-$C_3$ alkyl, or $C_{1-3}$ perfluoroalkyl. In some embodiments, $R^{51}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^A R^B$, $COR^A$, $CO_2 R^A$, OCORA, $NR^A COR^B$, $CONR^A R^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 8 or 9, in some embodiments $R^{52}$ is H, $C_1$-$C_3$ alkyl, or $C_{1-3}$ perfluoroalkyl. In some embodiments, $R^{52}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^A R^B$, $COR^A$, $CO_2 R^A$, OCORA, $NR^A COR^B$, $CONR^A R^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 8 or 9, in some embodiments $R^{53}$ is H, $C_1$-$C_3$ alkyl, or $C_{1-3}$ perfluoroalkyl. In some embodiments, $R^{53}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^A R^B$, $COR^A$, $CO_2 R^A$, OCORA, $NR^A COR^B$, $CONR^A R^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 8 or 9, in some embodiments $R^{54}$ is H, $C_1$-$C_3$ alkyl, or $C_{1-3}$ perfluoroalkyl. In some embodiments, $R^{54}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^A R^B$, $COR^A$, $CO_2 R^A$, OCORA, $NR^A COR^B$, $CONR^A R^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formulas 8 or 9, in some embodiments $R^{55}$ is H, $C_1$-$C_3$ alkyl, or $C_{1-3}$ perfluoroalkyl. In some embodiments, $R^{55}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^A R^B$, $COR^A$, $CO_2 R^A$, OCORA, $NR^A COR^B$, $CONR^A R^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formula 9, in some embodiments $R^{56}$ is H, $C_1$-$C_3$ alkyl, or $C_{1-3}$ perfluoroalkyl. In some embodiments, $R^{56}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^A R^B$, $COR^A$, $CO_2 R^A$, OCORA, $NR^A COR^B$, $CONR^A R^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formula 9, in some embodiments $R^{57}$ is H, $C_1$-$C_3$ alkyl, or $C_{1-3}$ perfluoroalkyl. In some embodiments, $R^{57}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^A R^B$, $COR^A$, $CO_2 R^A$, OCORA, $NR^A COR^B$, $CONR^A R^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formula 9, in some embodiments $R^{58}$ is H, $C_1$-$C_3$ alkyl, or $C_{1-3}$ perfluoroalkyl. In some embodiments, $R^{58}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^A R^B$, $COR^A$, $CO_2 R^A$, OCORA, $NR^A COR^B$, $CONR^A R^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formula 9, in some embodiments $R^{59}$ is H, $C_1$-$C_3$ alkyl, or $C_{1-3}$ perfluoroalkyl. In some embodiments, $R^{59}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, OCORA, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

With respect to any relevant structural representation, such as Formula 9, in some embodiments $R^{60}$ is H, $C_1$-$C_3$ alkyl, or $C_{1-3}$ perfluoroalkyl. In some embodiments, $R^{60}$ is H. Additionally, for any embodiments recited in this paragraph, all remaining relevant groups of $R^{1-60}$ may independently be $R^A$, F, Cl, CN, $OR^A$, $CF_3$, $NO_2$, $NR^AR^B$, $COR^A$, $CO_2R^A$, OCORA, $NR^ACOR^B$, $CONR^AR^B$; may independently be H; F; Cl; CN; $CF_3$; OH; $NH_2$; $C_{1-6}$ alkyl; $C_{1-6}$ amino; $C_{1-6}$ alkoxy; CHO; $C_{2-6}$—CO-alkyl; $CO_2H$; or $C_{2-6}$—$CO_2$-alkyl; may independently be H, $C_1$-$C_3$ alkyl, or $C_{1-3}$ perfluoroalkyl; or may be H.

In one embodiment, a host compound for use in emissive elements of organic light emitting devices is described, the compound being represented by Formula 10:

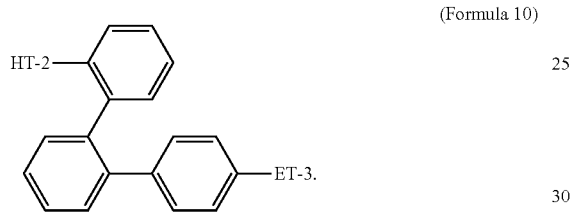

(Formula 10)

HT-2 can be optionally substituted carbazoyl, optionally substituted phenylcarbazolyl, optionally substituted (phenylcarbazolyl)phenyl, or optionally substituted phenylnaphthylamine; and ET-3 is an optionally substituted benzimidazol-2-yl, an optionally substituted bis(benzo[d]oxazol-2-yl)benz-1-yl, or an optionally substituted 3,5-bis(1-phenyl-1H-benzo[d]imidazol-2-yl)benz-1-yl.

In another embodiment, HT-2 can be:

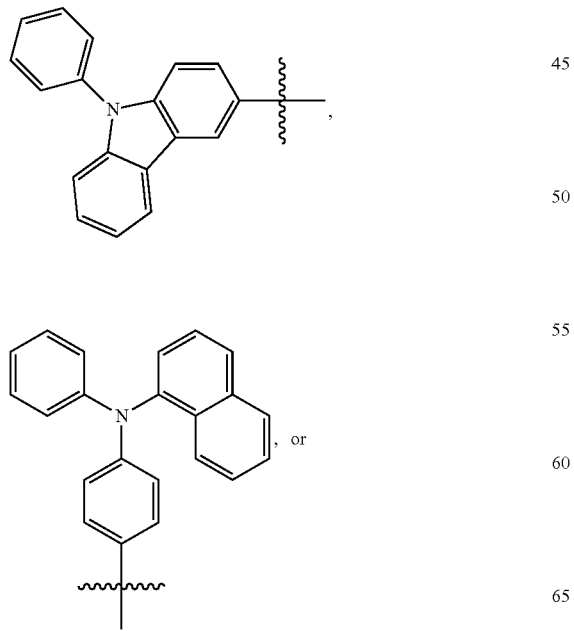

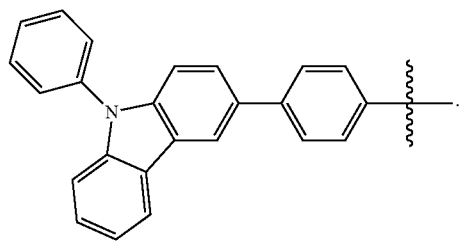

In another embodiment, ET-3 can be:

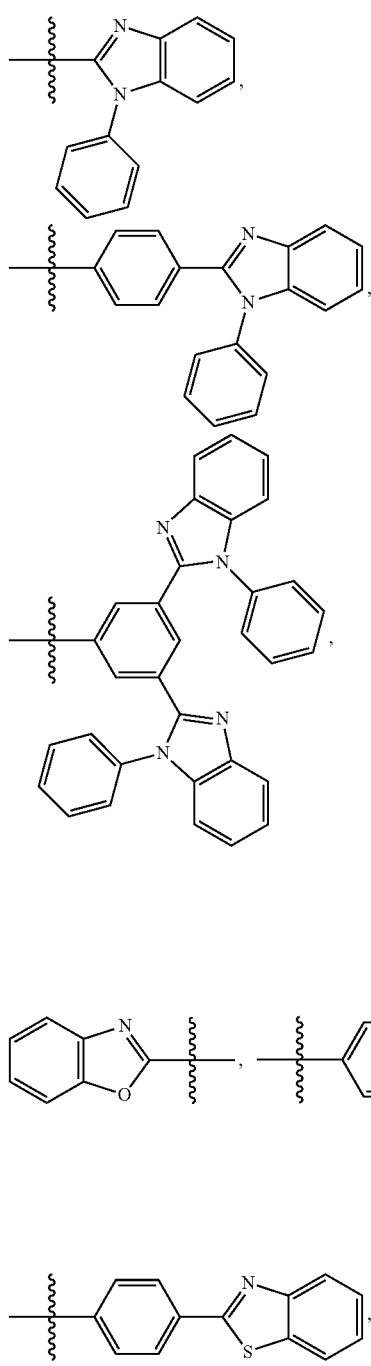

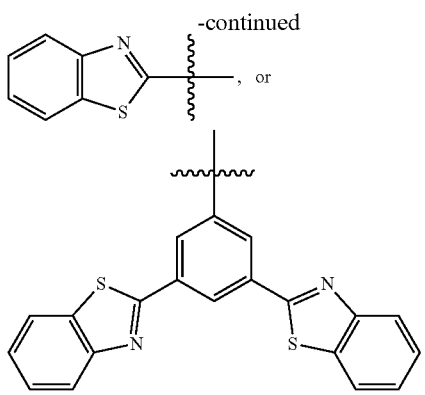, or

In one embodiment, a host compound for use in emissive elements of organic light emitting devices is described, the compound being represented by Formula 11:

(Formula 11)

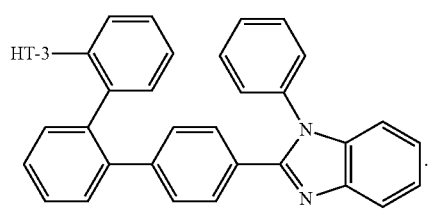

In another embodiment, HT-3 can be an optionally substituted cabazolyl, an optionally substituted phenylcarbazolyl or an optionally substituted phenylnaphthylaminophenyl.

In one embodiment, a host compound for use in emissive elements of organic light emitting devices is described, the compound being represented by Formula 12:

(Formula 12)

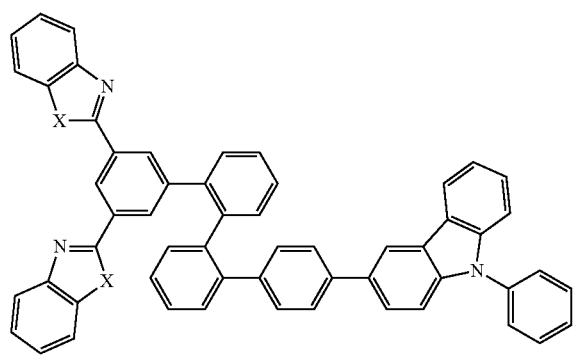

wherein X can be O, S or optionally substituted N.
In some embodiments, X can be

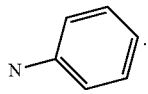

In other embodiments, the compound can be one of the following Hosts:

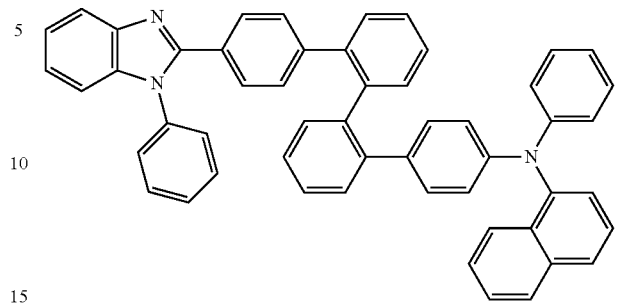

N-phenyl-N-(4'''-(1-phenyl-1H-benzo[d]imidazol-2-yl)-[1,1':2',1'':2'',1'''-quaterphenyl]-4-yl)naphthalen-1-amine (Host-1)

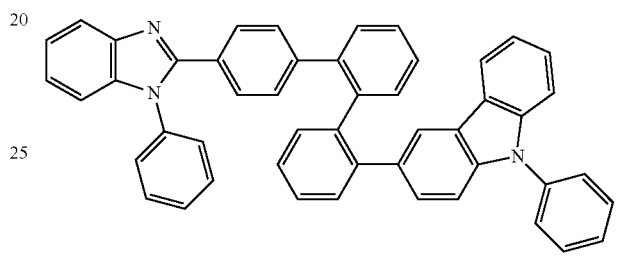

9-phenyl-3-(4''-(1-phenyl-1H-benzo[d]imidazol-2-yl)-[1,1':2',1''-terphenyl]-2-yl)-9H-carbazole (Host-2)

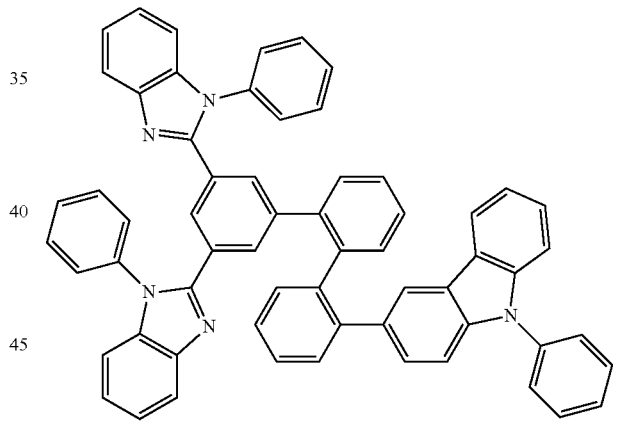

3-(3'',5''-bis(1-phenyl-1H-benzo[d]imidazol-2-yl)-[1,1':2',1''-terphenyl]-2-yl)-9-phenyl-9H-carbazole (Host-3)

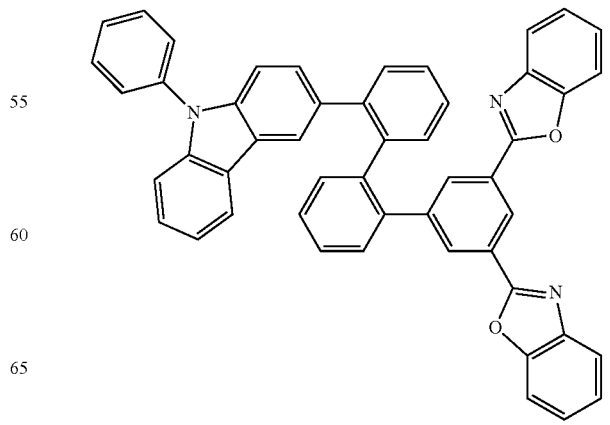

2,2'-(2"-(9-phenyl-9H-carbazol-3-yl)[1,1':2',1"-terphenyl]-3,5-diyl)bis(benzo[d]oxazole) (Host-4)

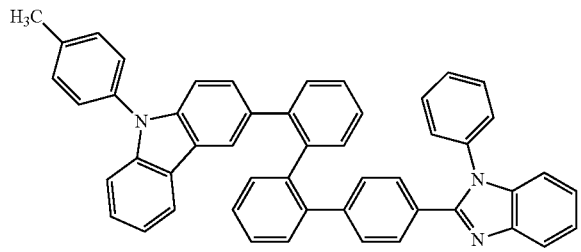 [SMILES: Cc1ccc(-n2c3ccccc3c3cc(-c4ccccc4-c4ccccc4-c4ccc(-c5nc6ccccc6n5-c5ccccc5)cc4)ccc32)cc1]

3-(4"-(1-phenyl-1H-benzo[d]imidazol-2-yl)-[1,1':2',1"-terphenyl]-2-yl)-9-(p-tolyl)-9H-carbazole (Host-5)

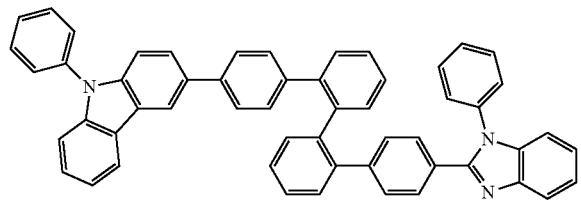 [SMILES: c1ccc(-n2c(-c3ccc(-c4ccccc4-c4ccccc4-c4ccc(-c5ccc6c(c5)c5ccccc5n6-c5ccccc5)cc4)cc3)nc3ccccc32)cc1]

9-phenyl-3-(4'''-(1-phenyl-1H-benzo[d]imidazol-2-yl)-[1,1':2',1":2",1'''-quaterphenyl]-4-yl)-9H-carbazole (Host-6)

In another embodiment, an emissive element is described comprising any of the aforementioned compounds.

In another embodiment, a device is described comprising any of the aforementioned compounds.

Figure 2:
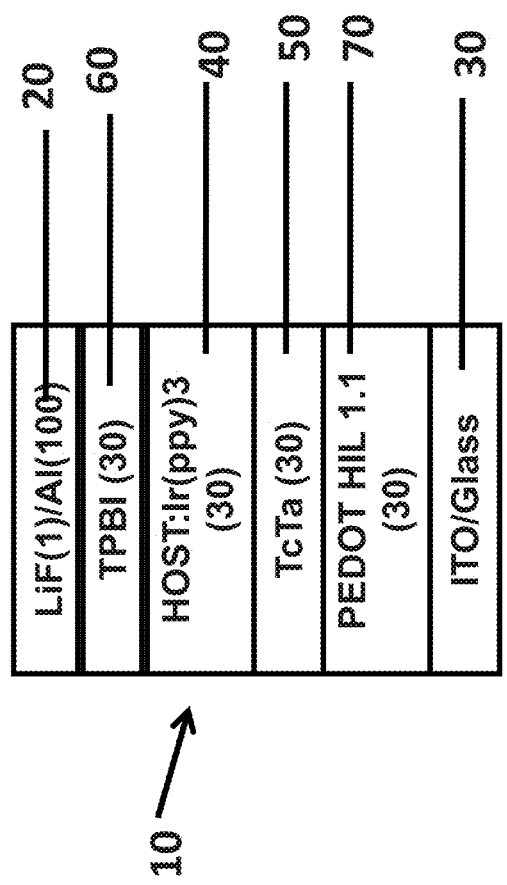
FIG. 2 is a schematic of a device incorporating an embodiment of a compound described herein.

As shown in FIGS. 1 and 2, there are shown embodiments of organic light emitting devices incorporating the compounds of the present application. The embodiments also provide an organic light-emitting diode device 10 comprising a cathode 20, an anode 30, a light-emitting layer 40 disposed between and electrically connected to the anode and the cathode, a hole-transport layer 50 between the anode and the light-emitting layer 40 and an electron-transport layer 60 between the cathode 30 and the light-emitting layer 40, wherein at least one of the light-emitting layer, the hole-transport layer and the electron-transport layer comprise a host compound described herein. In some embodiments, a hole injection layer 70 can be between the anode 20 and the hole transport layer 50.

An anode layer may comprise a conventional material such as a metal, mixed metal, alloy, metal oxide or mixed-metal oxide, or a conductive polymer. Examples of suitable metals include the Group 1 metals, the metals in Groups 4, 5, 6, and the Group 8-10 transition metals. If the anode layer is to be light-transmitting, mixed-metal oxides of Group 12, 13, and 14 metals or alloys thereof, such as Au, Pt, and indium-tin-oxide (ITO), may be used. The anode layer may include an organic material such as polyaniline, e.g., as described in "Flexible light-emitting diodes made from soluble conducting polymer," Nature, vol. 357, pp. 477-479 (11 Jun. 1992).

Examples of suitable high work function metals include but are not limited to Au, Pt, indium-tin-oxide (ITO), or alloys thereof. In some embodiments, the anode layer can have a thickness in the range of about 1 nm to about 1000 nm.

A cathode layer may include a material having a lower work function than the anode layer. Examples of suitable materials for the cathode layer include alkali metals of Group 1, Group 2 metals, Group 12 metals including rare earth elements, lanthanides and actinides, materials such as aluminum, indium, calcium, barium, samarium and magnesium, and combinations thereof. Li-containing organometallic compounds, LiF, and $Li_2O$ may also be deposited between the organic layer and the cathode layer to lower the operating voltage. Suitable low work function metals include but are not limited to Al, Ag, Mg, Ca, Cu, Mg/Ag, LiF/Al, CsF, CsF/Al or alloys thereof. In some embodiments, the cathode layer can have a thickness in the range of about 1 nm to about 1000 nm.

In some embodiments, the light-emissive layer may further comprise an emissive component or compound. The emissive component may be a fluorescent and/or a phosphorescent compound. In some embodiments, the emissive component comprises a phosphorescent material. In some embodiments, the emissive component may comprise a dopant. In some embodiments, the dopant is up to about 10% (w/w) of the host, or from about 0.1% (w/w) to about 5% (w/w) of the host.

The thickness of the light-emitting layer may vary. In some embodiments, the light-emitting layer has a thickness from about 20 nm to about 200 nm. In some embodiments, the light-emitting layer has a thickness in the range of about 20 nm to about 150 nm.

In some embodiments, the light-emitting layer can further include additional host material. Exemplary host materials are known to those skilled in the art. For example, the host material included in the light-emitting layer can be an optionally substituted compound selected from: an aromatic-substituted amine, an aromatic-substituted phosphine, a thiophene, an oxadiazole, 2-(4-biphenylyl)-5-(4-tert-butylphenyl)-1,3,4-oxadiazole (PBD), 1,3-bis(N,N-t-butyl-phenyl)-1,3,4-oxadiazole (OXD-7), a triazole, 3-phenyl-4-(1'-naphthyl)-5-phenyl-1,2,4-triazole (TAZ), 3,4,5-triphenyl-1,2,3-triazole, 3,5-bis(4-tert-butyl-phenyl)-4-phenyl[1,2,4]triazole, an aromatic phenanthroline, 2,9-dimethyl-4,7-diphenyl-phenanthroline (bathocuproine or BCP), 2,9-dimethyl-4,7-diphenyl-1,10-phenanthroline, a benzoxazole, a benzothiazole, a quinoline, aluminum tris(8-hydroxyquinolate) (Alq3), a pyridine, a dicyanoimidazole, cyano-substituted aromatic, 1,3,5-tris(2-N-phenylbenzimidazolyl)benzene (TPBI), 4,4'-bis[N-(naphthyl)-N-phenyl-amino]biphenyl (α-NPD), N,N'-bis(3-methylphenyl)N,N'-diphenyl-[1,1'-biphenyl]-4,4'-diamine (TPD), 4,4'-bis[N,N'-(3-tolyl)amino]-3,3'-dimethylbiphenyl (M14), 4,4'-bis[N,N'-(3-tolyl)amino]-3,3'-dimethylbiphenyl (HMTPD), 1,1-bis(4-bis(4-methylphenyl)aminophenyl)cyclohexane, a carbazole, 4,4'-N,N'-dicarbazole-biphenyl (CBP), poly(9-vinylcarbazole) (PVK), N,N'N"-1,3,5-tricarbazoloylbenzene (tCP), a polythiophene, a benzidine, N,N'-bis(4-butylphenyl)-N,N'-bis(phenyl)benzidine, a triphenylamine, 4,4',4"-tris(N-(naphthylen-2-yl)-N-phenylamino)triphenylamine, 4,4',4"-tris(3-methylphenylphenylamino)triphenylamine (MTDATA), a phenylenediamine, a polyacetylene, and a phthalocyanine metal complex.

In some embodiments, the light-emitting device may further comprise a hole-transport layer between the anode and the light-emitting layer and an electron-transport layer between the cathode and the light-emitting layer. In some embodiments, all of the light-emitting layer, the hole-transport layer and the electron-transport layer comprise the host compound described herein.

In some embodiments, the hole-transport layer may comprise at least one hole-transfer materials. Suitable hole-transport materials are known to those skilled in the art. Exemplary hole-transport materials include: 1,1-bis(4-bis(4-methylphenyl)aminophenyl)cyclohexane; 2,9-dimethyl-4,7-diphenyl-1,10-phenanthroline; 3,5-bis(4-tert-butyl-phenyl)-4-phenyl[1,2,4]triazole; 3,4,5-triphenyl-1,2,3-triazole; 4,4',4"-tris(N-(naphthylen-2-yl)-N-phenylamino)triphenylamine; 4,4',4'-tris(3-methylphenylphenylamino)triphenylamine (MTDATA); 4,4'-bis[N-(naphthyl)-N-phenyl-amino]biphenyl (α-NPD); 4,4'-bis[N,N'-(3-tolyl)amino]-3,3'-dimethylbiphenyl (HMTPD); 4,4'-bis[N,N'-(3-tolyl)amino]-3,3'-dimethylbiphenyl (M14); 4,4'-N,N'-dicarbazole-biphenyl (CBP); 1,3-N,N-dicarbazole-benzene (mCP); poly(9-vinylcarbazole) (PVK); a benzidine; a carbazole; a phenylenediamine; a phthalocyanine metal complex; a polyacetylene; a polythiophene; a triphenylamine; an oxadiazole; copper phthalocyanine; N,N'-bis(3-methylphenyl)N,N'-diphenyl-[1,1'-biphenyl]-4,4'-diamine (TPD); N,N'N"-1,3,5-tricarbazoloylbenzene (tCP); N,N'-bis(4-butylphenyl)-N,N'-bis(phenyl)benzidine; 4,4'-bis[N-(1-naphtyl)-N-phenylamino]biphenyl (NPB), 4,4'4"-tri(N-carbazolyl)triphenylamine (TcTa) and the like.

In some embodiments, the electron-transport layer may comprise at least one electron-transfer materials. Suitable electron transport materials are known to those skilled in the art. Exemplary electron transport materials that can be included in the electron transport layer are an optionally substituted compound selected from: aluminum tris(8-hydroxyquinolate) (Alq$_3$), 2-(4-biphenylyl)-5-(4-tert-butylphenyl)-1,3,4-oxadiazole (PBD), 1,3-bis(N,N-t-butyl-phenyl)-1,3,4-oxadiazole (OXD-7), 1,3-bis[2-(2,2'-bipyridine-6-yl)-1,3,4-oxadiazo-5-yl]benzene (BPY-OXD), 3-phenyl-4-(1'-naphthyl)-5-phenyl-1,2,4-triazole (TAZ), 2,9-dimethyl-4,7-diphenyl-phenanthroline (bathocuproine or BCP), and 1,3,5-tris[2-N-phenylbenzimidazol-z-yl]benzene (TPBI). In one embodiment, the electron transport layer is aluminum quinolate (Alq$_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI), or a derivative or a combination thereof.

If desired, additional layers may be included in the light-emitting device. Additional layers that may be included include an electron injection layer (EIL), hole blocking layer (HBL), exciton blocking layer (EBL), and/or hole injection layer (HIL). In addition to separate layers, some of these materials may be combined into a single layer.

In some embodiments, the light-emitting device can include an electron injection layer between the cathode layer and the light emitting layer. In some embodiments, the lowest un-occupied molecular orbital (LUMO) energy level of the material(s) that can be included in the electron injection layer is high enough to prevent it from receiving an electron from the light emitting layer. In other embodiments, the energy difference between the LUMO of the material(s) that can be included in the electron injection layer and the work function of the cathode layer is small enough to allow efficient electron injection from the cathode. A number of suitable electron injection materials are known to those skilled in the art. Examples of suitable material(s) that can be included in the electron injection layer include but are not limited to, an optionally substituted compound selected from the following: aluminum quinolate (Alq$_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI) a triazine, a metal chelate of 8-hydroxyquinoline such as tris(8-hydroxyquinoliate) aluminum, and a metal thioxinoid compound such as bis(8-quinolinethiolato) zinc. In one embodiment, the electron injection layer is aluminum quinolate (Alq$_3$), 2-(4-biphenylyl)-5-(4-tert-butylphenyl)-1,3,4-oxadiazole (PBD), phenanthroline, quinoxaline, 1,3,5-tris [N-phenylbenzimidazol-z-yl]benzene (TPBI), or a derivative or a combination thereof.

In some embodiments, the device can include a hole blocking layer, e.g., between the cathode and the light-emitting layer. Various suitable hole blocking materials that can be included in the hole blocking layer are known to those skilled in the art. Suitable hole blocking material(s) include, but are not limited to, an optionally substituted compound selected from the following: bathocuproine (BCP), 3,4,5-triphenyl-1,2,4-triazole, 3,5-bis(4-tert-butyl-phenyl)-4-phenyl-[1,2,4]triazole, 2,9-dimethyl-4,7-diphenyl-1,10-phenanthroline, and 1,1-bis(4-bis(4-methylphenyl)aminophenyl)-cyclohexane.

In some embodiments, the light-emitting device can include an exciton blocking layer, e.g., between the light-emitting layer and the anode. In one embodiment, the band gap of the material(s) that comprise exciton blocking layer is large enough to substantially prevent the diffusion of excitons. A number of suitable exciton blocking materials that can be included in the exciton blocking layer are known to those skilled in the art. Examples of material(s) that can compose an exciton blocking layer include an optionally substituted compound selected from the following: aluminum quinolate (Alq$_3$), 4,4'-bis[N-(naphthyl)-N-phenyl-amino]biphenyl (α-NPD), 4,4'-N,N'-dicarbazole-biphenyl (CBP), and bathocuproine (BCP), and any other material(s) that have a large enough band gap to substantially prevent the diffusion of excitons.

In some embodiments, the light-emitting device can include a hole injection layer, e.g., between the light-emitting layer and the anode. Various suitable hole injection materials that can be included in the hole injection layer are known to those skilled in the art. Exemplary hole injection material(s) include an optionally substituted compound selected from the following: a polythiophene derivative such as poly(3,4-ethylenedioxythiophene (PEDOT)/polystyrene sulphonic acid (PSS), a benzidine derivative such as N,N,N',N'-tetraphenylbenzidine, poly(N,N'-bis(4-butylphenyl)-N,N'-bis(phenyl)benzidine), a triphenylamine or phenylenediamine derivative such as N,N'-bis(4-methylphenyl)-N,N'-bis(phenyl)-1,4-phenylenediamine, 4,4',4"-tris(N-(naphthylen-2-yl)-N-phenylamino)triphenylamine, an oxadiazole derivative such as 1,3-bis(5-(4-diphenylamino)phenyl-1,3,4-oxadiazol-2-yl)benzene, a polyacetylene derivative such as poly(1,2-bis-benzylthio-acetylene), and a phthalocyanine metal complex derivative such as phthalocyanine copper. Hole-injection materials, while still being able to transport holes, may have a hole mobility substantially less than the hole mobility of conventional hole transport materials.

Those skilled in the art would recognize that the various materials described above can be incorporated in several different layers depending on the configuration of the device. In one embodiment, the materials used in each layer are selected to result in the recombination of the holes and electrons in the light-emitting layer.

Light-emitting devices comprising the compounds disclosed herein can be fabricated using techniques known in the art, as informed by the guidance provided herein. For example, a glass substrate can be coated with a high work functioning metal such as ITO which can act as an anode. After patterning the anode layer, a light-emitting layer that includes at least a compound disclosed herein can be deposited on the anode. The cathode layer, comprising a low work functioning metal (e.g., Mg:Ag), can then be vapor evaporated onto the light-emitting layer. If desired, the device can also include an electron transport/injection layer, a hole blocking layer, a hole injection layer, an exciton blocking layer and/or a second light-emitting layer that can be added to the device using techniques known in the art, as informed by the guidance provided herein.

EXAMPLES

Example 1

Luminescent Dye

Synthesis of Bipolar Hosts

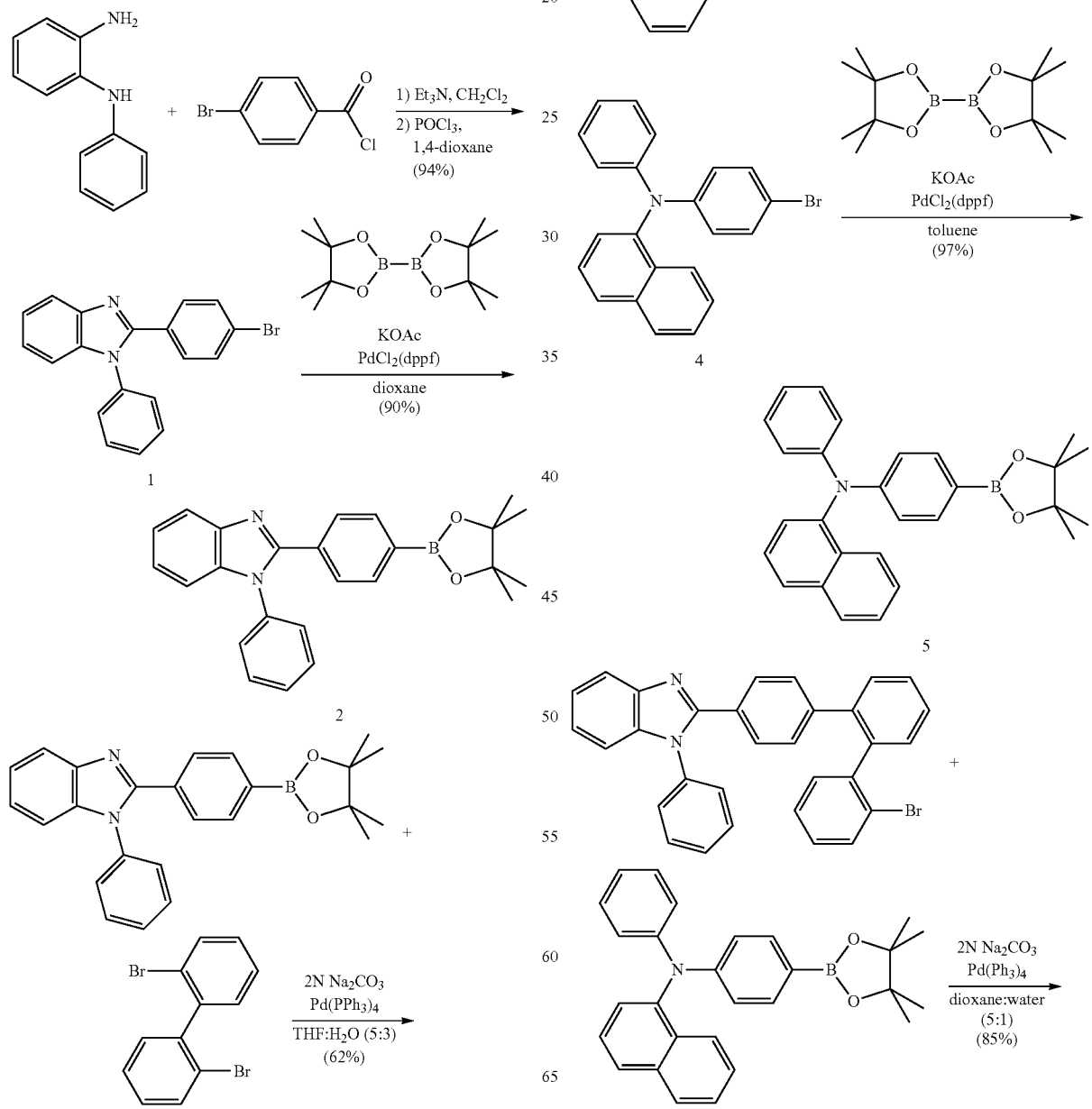

-continued

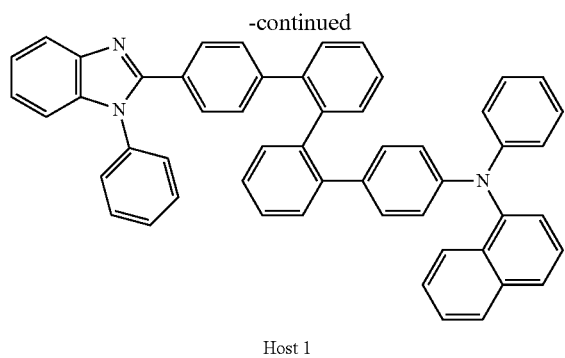

Host 1

2-(4-bromophenyl)-1-phenyl-1H-benzo[d]imidazole (Compound 1)

Compound 1 (Ge, Z.; Hayakawa, T.; Ando, S.; Ueda, M.; Akiike, T.; Miyamoto, H.; Kajita, T.; Kakimoto, M. *Chem. Mater.* 2008, 20(7), 2532-2537) was prepared as follows: to a chilled (ca. 0° C.), stirring solution of N-phenyl-o-phenylene-1,2-diamine (21.41 g, 116.2 mmol) in anhydrous dichloromethane ($CH_2Cl_2$) (575 mL) was added 4-bromobenzoyl chloride (25.00 g, 113.9 mmol) portion-wise, followed by dropwise addition of triethylamine ($Et_3N$) (31.8 mL). The reaction was allowed to warm to room temperature and stirring continued until TLC ($SiO_2$, 4:1 hexanes-ethyl acetate) indicated consumption of the starting material. Upon completion, the reaction was washed with water and brine, dried over $MgSO_4$, filtered and concentrated in vacuo. The resulting crude was then dissolved in anhydrous 1,4-dioxane (500 mL) and heated to about 80° C. Upon completely dissolving, phosphorus oxychloride (31.2 mL, 335 mmol) was added to the solution slowly via syringe and the reaction then maintained at about 115° C. Upon completion (ca. 1 h), the solution was cooled to room temperature (RT) and poured over $CH_2Cl_2$ (ca. 3 L) and washed with brine. The organics were then dried over $MgSO_4$, filtered and concentrated in vacuo. Purification of the crude product by recrystallization from $CH_2Cl_2$ and hexanes provided Compound 1 (37.5 g, 94%) as an off-white solid: confirmed by LCMS (APCI): calculated for $C_{19}H_{13}BrN_2$ (M+): 349; Found: 349.

1-phenyl-2-(4-(4,4,5,5-tetramethyl-1,3,2-dioxaborolan-2-yl)phenyl)-1H-benzo[d]imidazole (Compound 2)

A procedure from the literature [Ge, Z.; Hayakawa, T.; Ando, S.; Ueda, M.; Akiike, T.; Miyamoto, H.; Kajita, T.; Kakimoto, M. *Chem. Mater.* 2008, 20(7), 2532-2537] was modified as follows: a mixture of Compound 1 (36.00 g, 103.1 mmol), bis(pinacolato)diboron (28.80 g, 113.4 mmol), [1,1'-bis(diphenylphosphino)-ferrocene]dichloropalladium (II) (3.771 g, 5.154 mmol), potassium acetate (30.35 g, 309.3 mmol) and 1,4-dioxane (480 mL) was degassed with argon for about 1 h at about 40° C. while stirring. The reaction mixture was then maintained at about 80° C. while stirring. Upon confirming consumption of the starting material by TLC ($SiO_2$, 9:1 hexanes-ethyl acetate), the reaction was cooled to RT and poured over ethyl acetate (EtOAc) (ca. 1.6 L). The mixture was then filtered through a short silica gel plug (ca. ½ inch) and the filtrant washed copiously with EtOAc (ca. 200 mL). The combined organics were then washed with sat. $NaHCO_3$, water and brine, dried over $MgSO_4$, filtered and concentrated in vacuo. Purification of the crude product via flash chromatography ($SiO_2$, 4:1 to 1:1-hexanes:ethyl acetate) afforded Compound 2 (36.8 g, 90%) as an off-white powder: confirmed by LCMS (APCI): calculated for $C_{25}H_{26}BN_2O_2$ (M+H+): 397; Found: 397.

2-(2"-bromo-[1,1':2',1"-terphenyl]-4-yl)-1-phenyl-1H-benzo[d]imidazole (Compound 3)

A mixture of Compound 2 (3.00 g, 7.57 mmol), 2,2'-dibromo-1,1'-biphenyl (4.72 g, 15.1 mmol), tetrakis(triphenylphosphine)palladium(0) (0.350 g, 0.303 mmol), $Na_2CO_3$ (3.18 g, 30.0 mmol), $H_2O$ (30 mL) and tetrahydrofuran (THF) (50 mL) was degassed with argon for about 44 min while stirring. The reaction mixture was then maintained under argon at about 80° C. while stirring. Upon confirming consumption of the starting material by TLC ($SiO_2$, 19:1-$CH_2Cl_2$:acetone), the reaction was cooled to RT and poured over $CH_2Cl_2$ (ca. 250 mL). The organics were then washed with $H_2O$ and brine, dried over $MgSO_4$, filtered and concentrated in vacuo. The crude product was purified via flash chromatography ($SiO_2$, 100% $CH_2Cl_2$ to 39:1-$CH_2Cl_2$:acetone) to yield Compound 3 (2.34 g, 62%) as an off-white foam: confirmed by LCMS (APCI): calculated for $C_{31}H_{21}BrN_2$ (M+): 501; Found: 501.

N-(4-bromophenyl)-N-phenylnaphthalen-1-amine (Compound 4)

Compound 4 [Xu, H.; Yin, K.; Huang, W. *Chem. Eur. J.* 2007, 13(36), 10281-10293] was prepared as follows: a mixture of N-phenylnaphthalen-1-amine (2.767 g, 12.62 mmol), 1-bromo-4-iodobenzene (7.140 g, 25.24 mmol), tris(dibenzylideneacetone)dipalladium(0) (0.578 g, 0.631 mmol), tri-tert-butylphosphine (10 wt. % in hexanes) (5.83 mL, 1.89 mmol), sodium tert-butoxide (NaOtBu) (3.032 g, 31.55 mmol) and anhydrous toluene (80 mL) was degassed with argon for about 40 min while stirring. The reaction mixture was then maintained under argon at about 85° C. while stirring. Upon confirming consumption of the starting material by TLC ($SiO_2$, 100% hexanes), the reaction was cooled to RT and poured over EtOAc (ca. 300 mL). The organics were then washed with sat. $NaHCO_3$, $H_2O$ (2×) and brine, dried over $MgSO_4$, filtered and concentrated in vacuo. Purification of the crude product via flash chromatography ($SiO_2$, 8:1-hexanes:$CH_2Cl_2$) provided Compound 4 (2.93 g, 62%) as a white foam: confirmed by LCMS (APCI): calculated for $C_{22}H_{16}BrN$ (M+): 374; Found: 374.

N-phenyl-N-(4-(4,4,5,5-tetramethyl-1,3,2-dioxaborolan-2-yl)phenyl)naphthalen-1-amine (Compound 5)

Compound 5 [Shin, D.; Paek, W.; Choi, B.; Kwon, O.; Kim, M.; Son, Y.; Han, E.; Song, J. U.S. Pat. Appl. Publ., 20070276160, 29 Nov. 2007] was prepared as follows: a mixture of Compound 4 (2.54 g, 6.79 mmol), bis(pinacolato) diboron (3.62 g, 14.3 mmol), [1,1'-bis(diphenylphosphino)-ferrocene]dichloropalladium(II) (0.298 g, 0.407 mmol), potassium acetate (2.00 g, 20.4 mmol) and anhydrous toluene (50 mL) was degassed with argon for about 28 min while stirring. The reaction mixture was then maintained under argon at about 100° C. while stirring. Upon confirming consumption of the starting material by TLC ($SiO_2$, 4:1 hexanes-$CH_2Cl_2$), the reaction was cooled to RT and poured over EtOAc (ca. 200 mL). The organics were then washed with sat. $NaHCO_3$, water and brine, dried over $MgSO_4$, filtered and concentrated in vacuo. Purification of the crude product via flash chromatography ($SiO_2$, 2:1 to 3:2-hexanes: $CH_2Cl_2$ to 100% CH$_2$Cl$_2$) yielded Compound 5 (2.78 g, 97%) as a colorless foam: confirmed by LCMS (APCI): calculated for C$_{28}$H$_{29}$BNO$_2$ (M+H$^+$): 422; Found: 422.

N-phenyl-N-(4'''-(1-phenyl-1H-benzo[d]imidazol-2-yl)-[1,1':2',1'':2'',1'''-quaterphenyl]-4-yl)naphthalen-1-amine (Host-1)

A mixture of Compound 5 (0.588 g, 1.40 mmol), Compound 3 (0.700 g, 1.40 mmol), tetrakis(triphenylphosphine)palladium(0) (64.5 mg, 55.8 μmol), Na$_2$CO$_3$ (0.530 g, 5.00 mmol), H$_2$O (5 mL) and 1,4-dioxane (25 mL) was degassed with argon for about 18 min while stirring. The reaction mixture was then maintained under argon at about 110° C. while stirring. Upon confirming consumption of the starting material by LCMS, the reaction was cooled to RT and poured over CH$_2$Cl$_2$ (ca. 300 mL). The organics were then washed with H$_2$O and brine, dried over MgSO$_4$, filtered and concentrated in vacuo. The crude product was purified via flash chromatography (SiO$_2$, 17:3-hexanes: acetone) and recrystallization from CH$_3$OH to afford Host-1 (0.97 g, 85%) as an off-white solid: confirmed by LCMS (APCI): calculated for C$_{53}$H$_{37}$N$_3$ (M$^+$): 716; Found: 716.

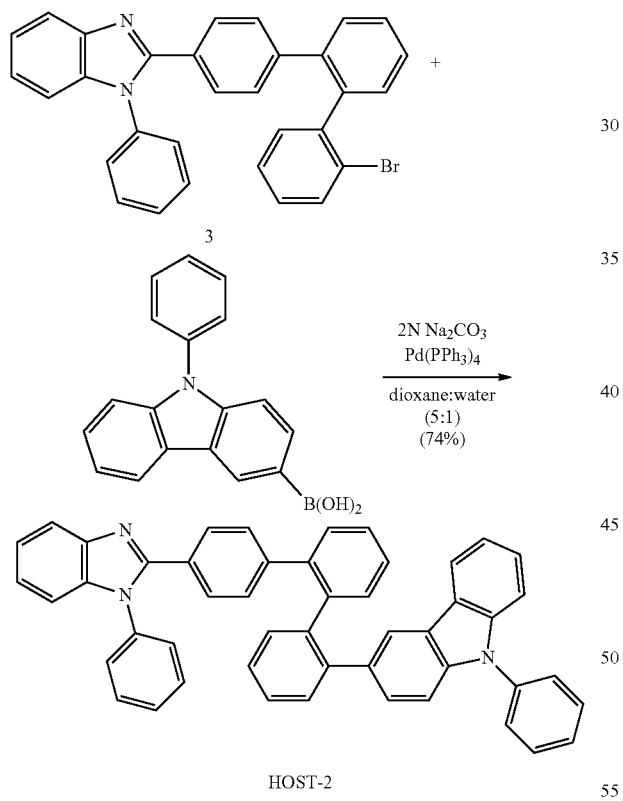

9-phenyl-3-(4''-(1-phenyl-1H-benzo[d]imidazol-2-yl)-[1,1':2',1''-terphenyl]-2-yl)-9H-carbazole (Host-2)

Following the procedure for Host-1, (9-phenyl-9H-carbazol-3-yl)boronic acid (0.458 g, 1.60 mmol), Compound 3 (0.800 g, 1.60 mmol), tetrakis(triphenylphosphine)palladium(0) (73.7 mg, 63.8 μmol), Na$_2$CO$_3$ (0.530 g, 5.00 mmol), H$_2$O (5 mL) and 1,4-dioxane (25 mL) provided Host-2 (0.78 g, 74%) as an off-white solid after flash chromatography (SiO$_2$, 17:3-hexanes: acetone) and recrystallization from methanol (CH$_3$OH): confirmed by LCMS (APCI): calculated for C$_{49}$H$_{33}$N$_3$ (M$^+$): 664; Found: 664.

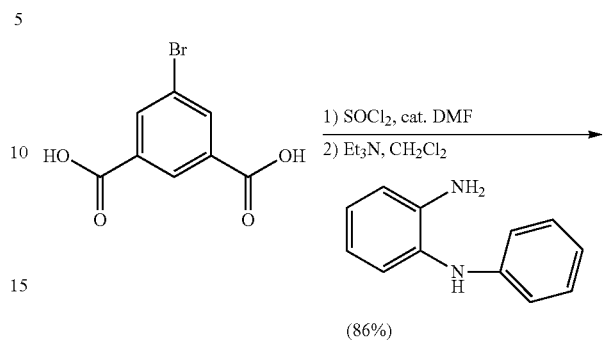

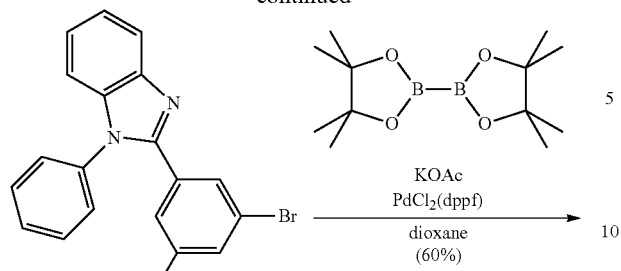
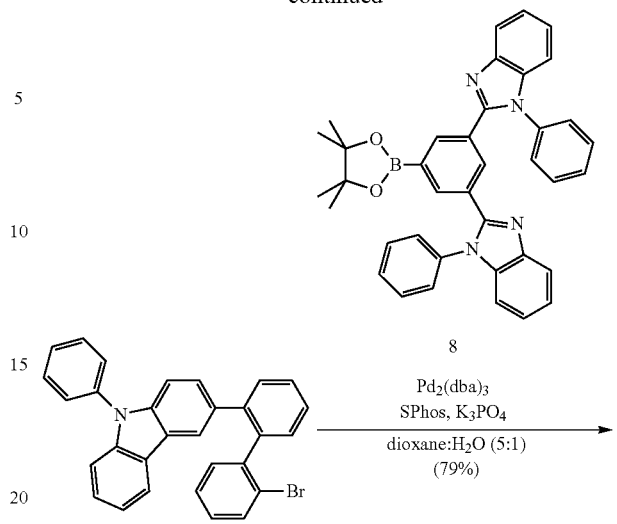
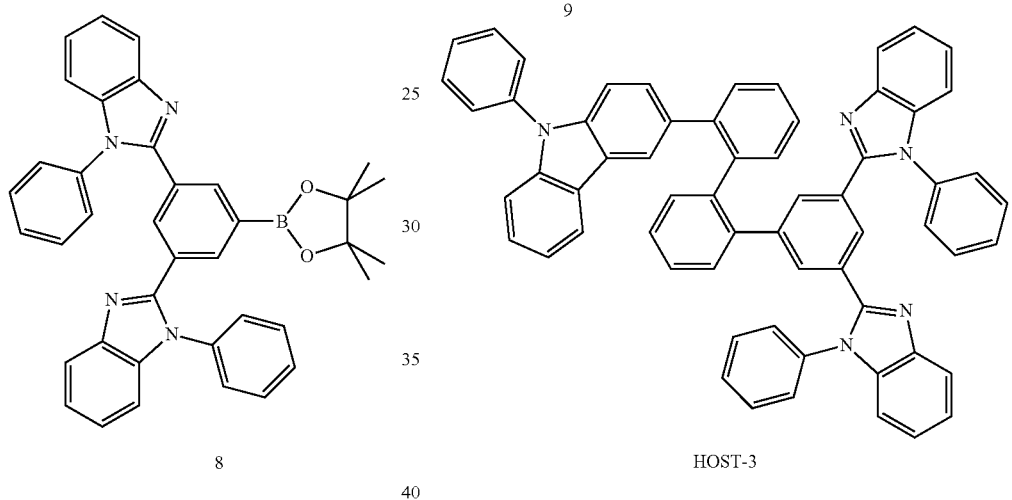
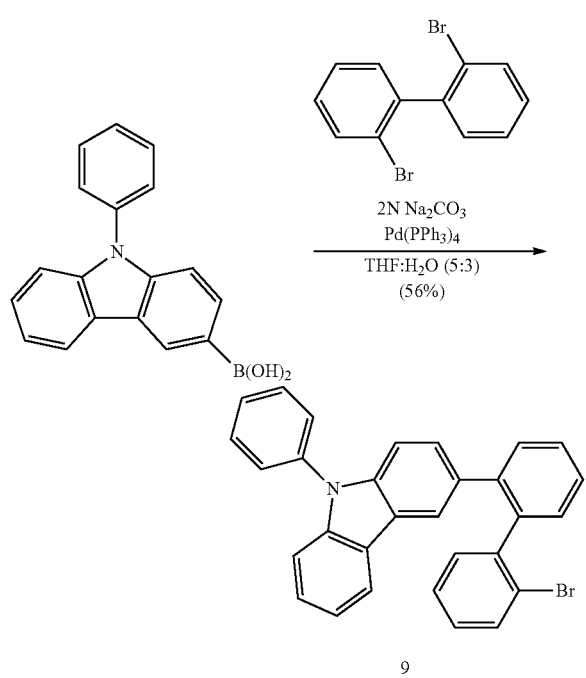

5-Bromo-N1,N3-bis(2-(phenylamino)phenyl)isophthalamide (Compound 6)

A mixture of 5-bromoisophthalic acid (15.0 g, 61.2 mmol) in thionyl chloride (60 mL) with 0.2 mL dimethylformamide (DMF) was heated to reflux overnight under argon. After removing the excess thionyl chloride under reduced pressure, the remaining liquid was dissolved in anhydrous $CH_2Cl_2$ (200 mL). To the solution was added N-phenyl-o-phenyldiamine (22.5 g, 122 mmol), followed by slow addition of triethylamine (22.2 mL, 159 mmol) with ice-bath cooling. The mixture was allowed to warm to RT overnight. The resulting suspension was then diluted with $CH_2Cl_2$ (200 mL), filtered and the filtrant washed with $CH_2Cl_2$ to provide Compound 6 (30.3 g, 86%) as an off-white solid: confirmed by LCMS (APCI): calculated for $C_{32}H_{25}BrN_4O_2$ (M$^+$): 577; Found: 577.

2,2'-(5-bromo-1,3-phenylene)bis(1-phenyl-1H-benzo[d]imidazole) (Compound 7)

To a suspension of Compound 6 (30 g, 52 mmol) in anhydrous 1,4-dioxane (300 mL), $POCl_3$ (30.6 g, 18.6 mL, 200 mmol) was added slowly with water bath cooling. The resulting mixture was then maintained at 100° C. After cooling to room temperature, the mixture was poured into ice (ca. 300 g) and neutralized with Na$_2$CO$_3$, followed by extraction with CH$_2$Cl$_2$ (2×300 mL). The organic phase was then washed with brine, dried over Na$_2$SO$_4$ and concentrated in vacuo. To the mixture, acetonitrile (300 mL) was added and stirred, then filtered. The solid was collected and recrystallized in CH$_2$Cl$_2$/hexane to afford a white solid (18.9 g). The filtrant was purified by flash chromatography (SiO$_2$, 100% hexanes to 9:1 to 4:1-hexanes/ethyl acetate). The main fraction was collected and concentrated to give additional product, white solid (5.17 g). Total amount is 24.1 g (86%): confirmed by LCMS (APCI): calculated for C$_{32}$H$_{21}$BrN$_4$ (M$^+$): 541; Found: 541.

2,2'-(5-(4,4,5,5-tetramethyl-1,3,2-dioxaborolan-2-yl)-1,3-phenylene)bis(1-phenyl-1H-benzo[d]imidazole) (Compound 8)

A mixture of Compound 7 (10.0 g, 18.5 mmol), bis(pinacolato)diboron (5.0 g, 20 mmol), PdCl$_2$(dppf) (0.50 g, 0.68 mmol) and potassium acetate (10.0 g, 102 mmol) in anhydrous 1,4-dioxane (300 mL) was degassed with Ar and maintained at about 80° C. for about 30 hours. The mixture was then poured over ethyl acetate (300 mL) and the organics washed with brine, dried over Na$_2$SO$_4$ and concentrated in vacuo. Purification of the crude by flash chromatography (SiO$_2$, 7:3-hexanes:CH$_2$Cl$_2$) afforded Compound 8 (6.58 g, 60%) as a light yellow solid: confirmed by LCMS (APCI): calculated for C$_{38}$H$_{34}$BN$_4$O$_2$ (M+H$^+$): 589; Found: 589.

3-(2'-bromo-[1,1'-biphenyl]-2-yl)-9-phenyl-9H-carbazole (Compound 9)

Following the procedure for Compound 3, (9-phenyl-9H-carbazol-3-yl)boronic acid (1.84 g, 6.41 mmol), 2,2'-dibromo-1,1'-biphenyl (4.00 g, 12.8 mmol), tetrakis(triphenylphosphine)palladium(0) (0.296 g, 0.257 mmol), Na$_2$CO$_3$ (2.54 g, 24.0 mmol), H$_2$O (24 mL) and THF (40 mL) yielded Compound 9 (1.69 g, 56%) as a colorless solid after flash chromatography (SiO$_2$, 19:1-hexanes: CH$_2$Cl$_2$): confirmed by LCMS (APCI): calculated for C$_{30}$H$_{20}$NBr (M$^+$): 474; Found: 474.

3-(3",5"-bis(1-phenyl-1H-benzo[d]imidazol-2-yl)-[1,1':2',1"-terphenyl]-2-yl)-9-phenyl-9H-carbazole (Host-3)

Following the procedure for Host-1, Compound 8 (0.992 g, 1.69 mmol), Compound 9 (0.800 g, 1.69 mmol), tetrakis(triphenylphosphine)palladium(0) (77.9 mg, 67.5 μmol), Na$_2$CO$_3$ (0.530 g, 5.00 mmol), H$_2$O (5 mL) and 1,4-dioxane (25 mL) yielded Host-3 (1.15 g, 79%) as an off-white solid after flash chromatography (SiO$_2$, 100% CH$_2$Cl$_2$ to 19:1-CH$_2$Cl$_2$:acetone): confirmed by LCMS (APCI): calculated for C$_{62}$H$_{41}$N$_5$ (M$^+$): 856; Found: 856.

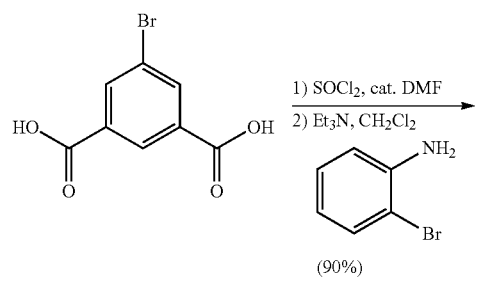

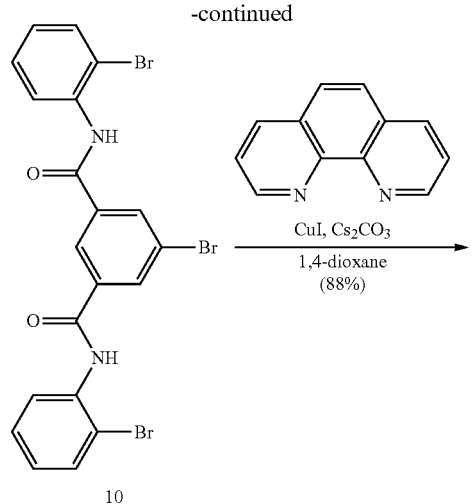

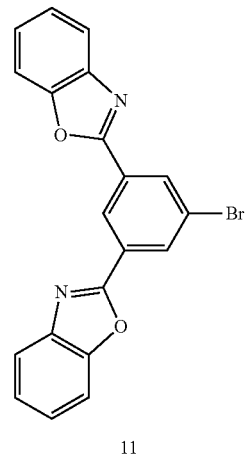

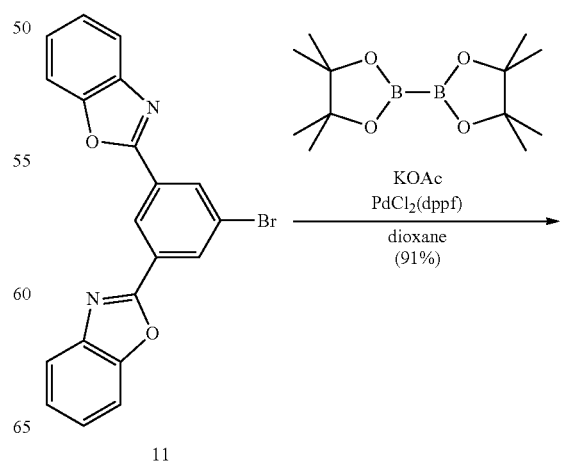

-continued

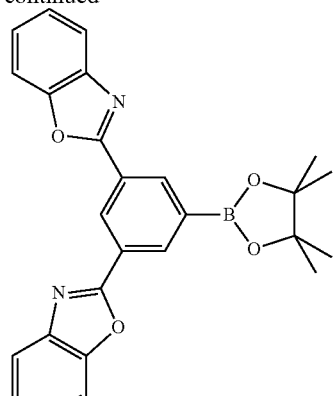

12

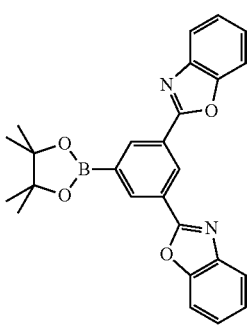

HOST-4

5-bromo-N1,N3-bis(2-bromophenyl)isophthalamide (Compound 10)

A mixture of 5-bromoisophthalic acid (10.0 g, 40.8 mmol) and cat. DMF (5 drops) in thionyl chloride (40 mL, 551 mmol) was heated to reflux under Ar overnight. After removal of the excess thionyl chloride under vacuum, the crude intermediate was dissolved in anhydrous $CH_2Cl_2$ (200 mL). To the chilled (0° C.) solution was added 2-bromoaniline (14.0 g, 81.6 mmol), followed by dropwise addition of triethylamine (15 mL). The resulting mixture was then stirred overnight and allowed to warm to RT. The suspension was then filtered and the filtrant washed with $CH_2Cl_2$ to afford crude Compound 10 (20.3 g, 90%) as an off-white solid: confirmed by LCMS (APCI): calculated for $C_{20}H_{13}Br_3N_2O_2$ ($M^+$): 553; Found: 553.

2,2'-(5-bromo-1,3-phenylene)bis(benzo[d]oxazole) (Compound 11)

A mixture of Compound 10 (20.3 g, 36.7 mmol), CuI (0.700 g, 3.67 mmol), $Cs_2CO_3$ (23.9 g, 73.5 mmol), 1,10-phenanthroline (1.32 g, 7.35 mmol) and 1,4-dioxane (300 mL) was degassed with Ar and then maintained at about 120° C. overnight. Upon confirming consumption of the starting material by TLC ($SiO_2$, 4:1 hexanes-ethyl acetate), the reaction was cooled to RT and diluted with EtOAc (ca. 300 mL) and $H_2O$ (ca. 400 mL). The resulting suspension was then filtered and the filtrant washed copiously with $H_2O$ and $CH_3OH$ to provide Compound 11 (12.7 g, 88%) as an off-white solid: confirmed by LCMS (APCI): calculated for $C_{20}H_{11}BrN_2O_2$ ($M^+$): 391; Found: 391.

2,2'-(5-(4,4,5,5-tetramethyl-1,3,2-dioxaborolan-2-yl)-1,3-phenylene)bis(benzo[d]oxazole) (Compound 12)

A mixture of Compound 11 (10.0 g, 25.6 mmol), bis(pinacolato)diboron (7.14 g, 28.1 mmol), [1,1'-bis(diphenylphosphino)-ferrocene]dichloropalladium(II) (0.935 g, 1.28 mmol), potassium acetate (7.53 g, 76.7 mmol) and 1,4-dioxane (125 mL) was degassed with Ar and then maintained under Ar at about 80° C. while stirring. Upon confirming consumption of the starting material by TLC ($SiO_2$, 4:1 hexanes-ethyl acetate), the reaction was cooled to RT and poured over EtOAc and brine. The mixture was then filtered and the filtrant washed copiously with $H_2O$ to afford Compound 12 (10.2 g, 91%) as a grey solid: confirmed by LCMS (APCI): calculated for $C_{26}H_{24}BN_2O_4$ ($M+H^+$): 439; Found: 439.

2,2'-(2''-(9-phenyl-9H-carbazol-3-yl)[1,1':2',1''-terphenyl]-3,5-diyl)bis(benzo[d]oxazole) (Host-4)

Following the procedure for Host-1, Compound 9 (0.800 g, 1.69 mmol), Compound 12 (0.739 g, 1.69 mmol), tetrakis(triphenylphosphine)palladium(0) (77.9 mg, 67.5 µmol), $Na_2CO_3$ (0.530 g, 5.00 mmol), $H_2O$ (5 mL) and 1,4-dioxane (25 mL) yielded Host-4 (0.89 g, 75%) as an off-white solid after flash chromatography ($SiO_2$, 1:1 to 3:1 to 9:1-$CH_2Cl_2$: hexanes): confirmed by LCMS (APCI): calculated for $C_{50}H_{32}N_3O_2$ ($M+H^+$): 707; Found: 707.

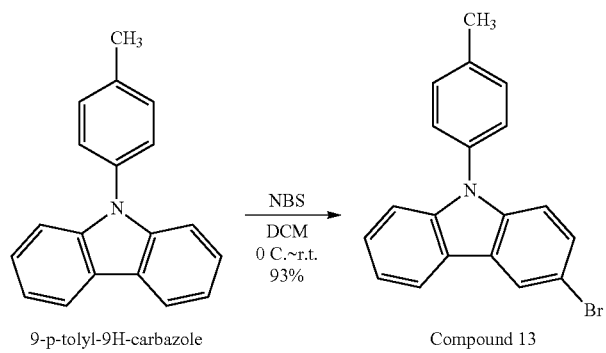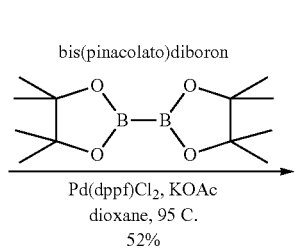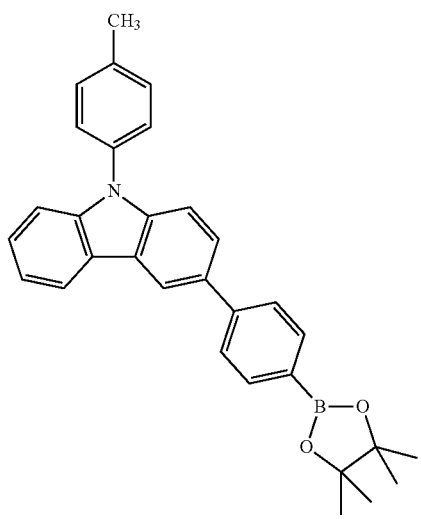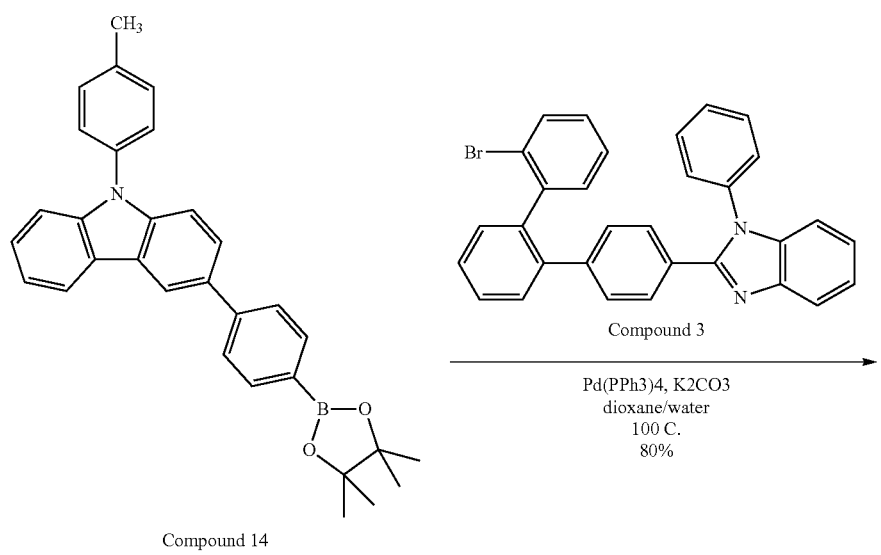

-continued

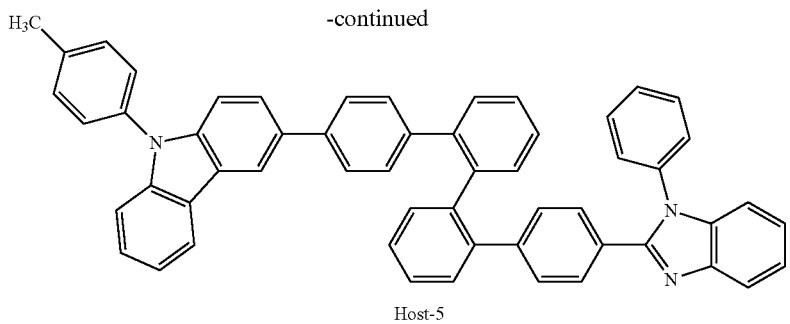

Host-5

3-bromo-9-(p-tolyl)-9H-carbazole (Compound 13)

To a solution of 9-p-tolyl-9H-carbazole (0.82 g, 3.2 mmol) in dichloromethane (DCM)(30 mL) was added N-bromosuccinimide (NBS) at about 0° C. The whole was stirred at about 0° C. to about room temperature (RT) overnight. The resulting solution was purified by flash column (silica gel, hexanes to hexanes/dichloromethane 8:1). After removal of solvent, a white solid (Compound 13) was obtained (1.0 gram, in 93% yield).

3-(4,4,5,5-tetramethyl-1,3,2-dioxaborolan-2-yl)-9-(p-tolyl)-9H-carbazole (Compound 14): The mixture of 3-bromo-9-(p-tolyl)-9H-carbazole (Compound 13)

(1.0 g, 3 mmol), bis(pinacolato)diboron (0.838 g, 3.3 mmol), KOAc (0.588 g, 6 mmol) and Pd(dppf)Cl$_2$ (0.11 g, 0.15 mmol) in dioxane (20 mL), was degassed and heated at about 95° C. for about 5 hours. The resulting mixture was poured into ethyl acetate (200 mL), washed with brine, dried over Na$_2$SO$_4$, loaded on silica gel, and purified by flash column (silica gel, hexanes/dichloromethane 9:1 to 4:1 to 3:1). The desired fractions were collected, after removal of solvents, a white solid (Compound 14) was obtained (0.60 g, in 52% yield).

Host-5:

A mixture of 3-(4,4,5,5-tetramethyl-1,3,2-dioxaborolan-2-yl)-9-(p-tolyl)-9H-carbazole (Compound 14) (0.60 g, 1.57 mmol), 2-(2"-bromo-[1,1':2',1"-terphenyl]-4-yl)-1-phenyl-1H-benzo[d]imidazole (Compound 3) (0.78 g, 1.57 mmol), Pd(PPh$_3$)$_4$ (0.092 g, 0.08 mmol) and Cs$_2$CO$_3$ (0.977 g, 3 mmol) in dioxane/water (50 mL/10 mL) was degassed and heated at about 100° C. overnight. The resulting mixture was poured into ethyl acetate (200 mL), washed with brine, dried over Na$_2$SO$_4$, loaded on silica gel and purified by flash column (hexanes/dichloromethane 4:1 to dichloromethane to dichloromethane/ethyl acetate 50:1). The desired fraction was collected, concentrated and recrystallized in dichloromethane/methanol to give a white solid (Host-5) (0.85 g, in 80% yield). Confirmed by LCMS (APCI+): calculated for C$_{50}$H$_{36}$N$_3$ (M+H): 678; Found: 678.

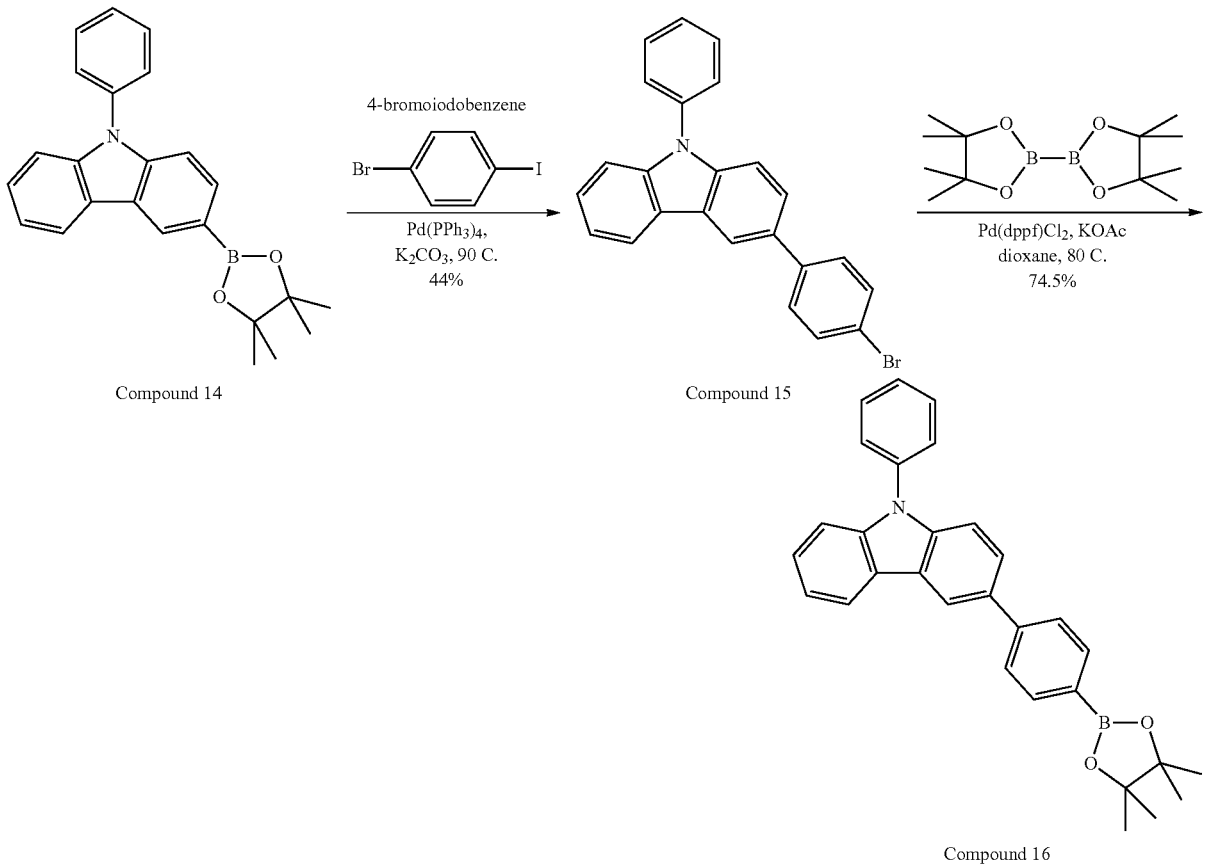

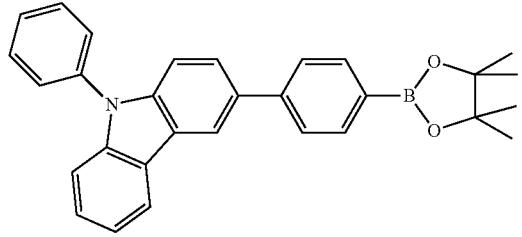
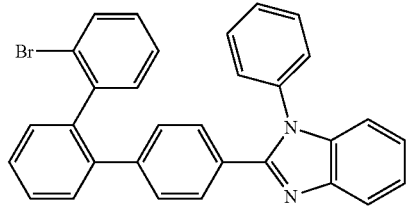

Compound 3

Pd(PPh3)4, K2CO3
dioxane/water
100 C.
62%

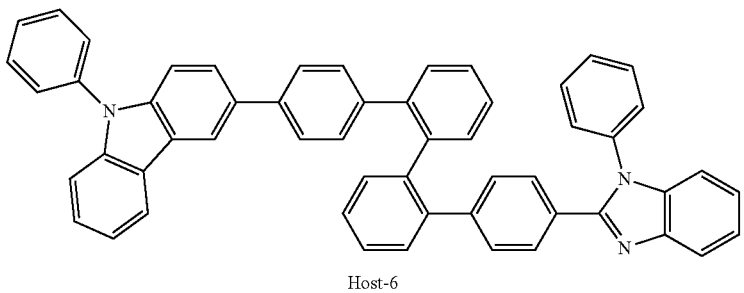

Host-6

3-(4-bromophenyl)-9-phenyl-9H-carbazole (Compound 15)

A mixture of 9-phenyl-3-(4,4,5,5-tetramethyl-1,3,2-dioxaborolan-2-yl)-9H-carbazole (Compound 14) (5.0 g, 13.5 mmol), 4-bromoiodobenzene (10.76 g, 38 mmol), Pd(PPh$_3$)$_4$ (0.5 g, 0.43 mmol) and potassium carbonate (K$_2$CO$_3$)(5.52 g, 40 mmol) in dioxane/water (80 mL/15 mL) was degassed and heated at about 100° C. overnight, then worked up with ethyl acetate/brine. The organic phase was collected, dried over Na$_2$SO$_4$, and purified by flash column (hexanes to hexane/ethyl acetate 90:1). The main fraction was collected, concentrated, and a precipitate was filtered to give a white solid (Compound 15) (2.35 g, in 44% yield). Confirmed by LCMS (APCI): calculated for C$_{24}$H$_{17}$BrN (M+H): 398; Found: 398.

9-phenyl-3-(4-(4,4,5,5-tetramethyl-1,3,2-dioxaborolan-2-yl)phenyl)-9H-carbazole (Compound 16)

a mixture of compound 19 (2.33 g, 5.85 mmol), bis(pinacolate)diborane (1.524 g, 6 mmol), Pd(dppf)Cl$_2$ (0.22 g, 0.3 mmol) and potassium carbonate (3.0 g, 30 mmol) in dioxane (100 mL) was degassed and heated at about 80° C. overnight. The mixture was worked up with ethyl acetate/brine and the organic phase was collected, dried over Na$_2$SO$_4$, purified by flash column (hexanes to hexane/ethyl acetate 90:1 to 40:1 to 30:1). The main fraction was collected, and white solid (Compound 20) was obtained after removal of solvent (1.94 g, in 74.5% yield). Confirmed by LCMS (APCI): calculated for C$_{30}$H$_{29}$BNO$_2$ (M+H): 446; Found: 446.

Host-6:

A mixture of compound 20 (0.70 g, 1.57 mmol), 2-(2"-bromo-[1,1':2',1"-terphenyl]-4-yl)-1-phenyl-1H-benzo[d]imidazole (Compound 3) (0.787 g, 1.57 mmol), Pd(PPh$_3$)$_4$ (0.115 g, 0.1 mmol) and Cs$_2$CO$_3$ (0.977 g, 3 mmol) in dioxane/water (50 mL/10 mL) was degassed and heated at about 100° C. overnight. The mixture was diluted with ethyl acetate (200 mL), washed with brine, dried over Na$_2$SO$_4$, loaded on silica gel and purified by flash column (hexanes/dichloromethane 4:1 to dichloromethane to dichloromethane/ethyl acetate 100:1). After removal of solvent, recrystallization in dichloromethane/methanol gave a white solid (Host-6) (0.72 g, in 62% yield). Confirmed by LCMS (APCI+): calculated for C$_{55}$H$_{38}$N$_3$ (M+H): 740; Found: 740.

Physical Properties of Hosts

Analytic Examples

Measuring Charge Mobility

The carrier mobility of an organic thin film was derived from the space charge limited current in the current-voltage (IV) measurement based on the Mott's steady state SCLC model $$J = \frac{9\varepsilon\varepsilon_0 \mu V^2}{8L^3}$$

where $\epsilon_0$ is the vacuum permittivity, $\epsilon$ is the relative permittivity of the organic layer, $\mu$ is the carrier mobility of the organic layer, V is the voltage bias and L is the thickness of the organic layer.

To evaluate the electron and hole mobility of an organic layer, single-carrier devices (electron-only and hole-only devices) were made. Electron-only devices may have Al/organic layer/LiF/Al structure with Al as the anode and LiF/Al as the cathode. The LiF/Al electrode has a low work function (~2.6 eV) which can facilitate the injection of electrons into the lower lying LUMO of the organic layer. By contrast, Al has a relatively lower work function (4.28 eV) than the HOMO (5~6 eV) of the organic layer being investigated, which prevents the hole injection from the anode. Thus, only electrons are injected into the organic layer and the electron mobility may be measured as the only charge carrier in the organic layer.

The hole-only devices may have the ITO/PEDOT/organic layer/Al with ITO as the anode and Al as the cathode. The high work function of PEDOT (5.2-5.4 eV) facilitates hole injection from the anode into the organic layer. By contrast, the work function (4.28 eV) of Al is higher than the LUMO of the organic layer (2~4 eV), which prevented electron injection from the cathode. Thus, only holes are injected into the organic layer, and the hole mobility may be measured as the only charge carrier in the organic layer.

Fabrication of electron-only device: A layer of Al was first deposited at a deposition rate of 0.3 nm/s upon a glass substrate (110 nm), the substrate having been cleaned by ultrasound in acetone, and consecutively in 2-propanol, then baked at 110° C. for about 3 hours, followed by treatment with oxygen plasma for about 30 min. In a glove-box hosted vacuum deposition system at a pressure of $10^{-7}$ torr (1 torr=133.322 Pa), Host-2 was then deposited on top of the Al layer at deposition rate of 0.1 nm/s, yielding a 100 nm thick film. LiF (1 nm) and Al (100 nm) were then deposited at a deposition rates of 0.015 nm/s and 0.3 nm/s, respectively.

Fabrication of hole-only device: the ITO coated glass substrate (110 nm) was cleaned by ultrasound in acetone, and consecutively in 2-propanol, baked at 110° C. for about 3 hours, followed by treatment with oxygen plasma for about 30 min. A layer of PEDOT: PSS (HIL 1.1 purchased from H.C. Starck) was spin-coated at 4000 rpm onto the pre-cleaned and $O_2$-plasma treated (ITO)-substrate and annealed at about 180° C. for about 10 min, yielding a thickness of around 30 nm. In a glove-box hosted vacuum deposition system at a pressure of $10^{-7}$ torr, Host-2 was first deposited on top of PEDOT/PSS layer at deposition rate of 0.1 nm/s, yielding a 100 nm thick film. Al was then deposited at a deposition rate of 0.3 nm/s. Each individual device had areas of about 0.08 $cm^2$.

Photoluminescence (PL) spectra were recorded on a FluoroMax-3 fluorescence spectrophotometer (Horiba Jobin Yvon, Edison, N.J., USA). 2-Methyltetrahydrofuran (2-MeTHF) (Aldrich, spectroscopic grade) was used as received. 2 M (2 mg of sample/1 mL of 2-MeTHF) was prepared and then transferred to quartz tube prior to measurement. Then, the sample was frozen by liquid nitrogen at 77K. A phosphorescent emission spectrum was recorded and the highest-energy vibronic band was determined to calculate triplet (T1) energy level.

Cyclic voltammetry (CV) experiments were performed with a μAuto-labII potentiostat (Eco Chemie [Metrohm Autolab B.V., Utrecht, the Netherlands]). All measurements were carried out at room temperature with a conventional three-electrode configuration, e.g., a glassy carbon working electrode, a platinum auxiliary electrode, and a nonaqueous Ag/AgCl reference electrode. A 15 mL $10^{-4}$ M HT-1 from 0.1M tetrabutylammonium hexafluorophosphate, $nBu_4PF_6$ DMF sample solution was prepared at room temperature and prior to measurement, the solution was purged under argon for 5 mins. Then anodic potential up to 1.6 V (enough potential to contain oxidation potential of HT-1) A 1.5 V potential was applied to this test sample resulting in a test sample oxidation potential [figure]. Scan rate used was 100 mV/s. About 1.0 mg of ferrocene/ferrocenium was then added to the test sample at the end of each measurement for calibration and the oxidation potential measured again. From these oxidation potential spectra, the $E_{1/2}$ values were determined as $\frac{1}{2}(E_p^a + E_p^c)$, where $E_p^a$ and $E_p^c$ are the anodic and cathodic peak potentials, respectively. HOMO (Highest occupied molecular orbital) energy was calculated by adding the determined shifted E½ value with reference to ferrocene (4.8 eV).

A 10 mL $10^{-6}$M analyte, e.g., Host-1, chloroform ($CHCl_3$) solution was analyzed with a Cary 50 spectrophotometer (Varian, Inc. [Agilent Technologies, Santa Clara, Calif., USA]). Analyzing an absorption as a function of wavelength plot provided an observed optical onset (eV), providing an estimated Optical band gap value, Eg (Opt). LUMO (lowest unoccupied molecular orbital) energy was determined from the relation, Eg (Opt)=HOMO−LUMO.

Subsequently, the values for Host-2, Host-3, and Host-4 were determined in a similar manner to that described in example immediately above. The results are reported below in Table 1.

TABLE 1

| | solution em peak (nm) | Film em peak (nm) | HOMO (eV) | LUMO (eV) | Tg (° C.) | T1 (eV) | $\mu_n$ | $\mu_e$ |
|---|---|---|---|---|---|---|---|---|
| Host-1 | 433 | 422 | −5.37 | −2.17 | 117 | 2.4 | $1.65 \times 10^{-5}$ | $3.0 \times 10^{-6}$ |
| Host-2 | 412 | 403 | −5.66 | −2.16 | 122 | 2.59 | $1.3 \times 10^{-7}$ | $5.4 \times 10^{-7}$ |
| Host-3 | 401 | 404 | −5.68 | −2.15 | 151 | 2.72 | $1.4 \times 10^{-7}$ | $1.2 \times 10^{-5}$ |
| Host-4 | 431 | 416 | −5.64 | −2.4 | 145 | 2.65 | $8.5 \times 10^{-6}$ | $4.7 \times 10^{-7}$ |

8.3 Device Configuration

Fabrication of Light-Emitting Device:

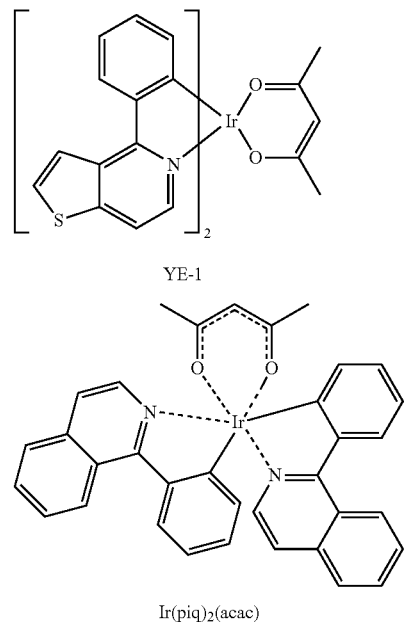

YE-1

Ir(piq)$_2$(acac)

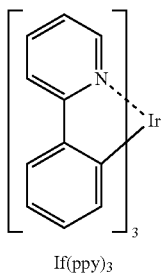

Ir(ppy)₃

A device as set forth in FIG. 1 was fabricated as follows. The ITO substrates having sheet resistance of about 14 ohm/sq were cleaned ultrasonically and sequentially in detergent, water, acetone and then IPA; and then dried in an oven at about 80° C. for about 30 min under ambient environment. Substrates were then baked at about 200° C. for about 1 hour in an ambient environment, then under UV-ozone treatment for about 30 minutes. PEDOT:PSS (hole-injection material) was then spin-coated onto the annealed substrate at about 4000 rpm for about 30 sec. The coated layer was then baked at about 100° C. for about 30 min in an ambient environment, followed by baking at about 200° C. for about 30 min inside a glove box (N₂ environment). The substrate was then transferred into a vacuum chamber, where N,N'-bis(naphthalen-1-yl)-N,N'-bis(phenyl)-2,2'-dimethylbenzidine (a-NPD [hole transporting material]) was vacuum deposited at a rate of about 0.1 nm/s under a base pressure of about 2×10⁻⁷ torr. YE-01 (10 wt %) was co-deposited as an emissive layer with Host-1 host material at about 0.01 nm/s and about 0.10 nm/s, respectively, to make the appropriate thickness ratio (about 30 nm). 1,3,5-tris(1-phenyl-1H-benzimidazol-)2-yl)benzene (TPBI) is then deposited at about 0.1 nm/s rate on the emissive layer, yielding a layer of about 30 nm. A layer of lithium fluoride (LiF) (electron injection material) was deposited at about 0.002 nm/s rate followed by deposition of the cathode as Aluminium (Al) at a rate of about 0.3 nm/s. The representative device structure was: ITO (about 150 nm thick)/PEDOT:PSS (about 30 nm thick)/NPB (about 30 nm thick)/Host-1:YE-01 (about 30 nm thick)/TPBI (about 30 nm thick)/LiF (about 1.0 nm thick)/Al (about 100 nm thick). The device was then encapsulated with a getter attached glass cap to cover the emissive area of the OLED device in order to protect from moisture, oxidation or mechanical damage.

Device B (FIG. 2) was constructed in a similar to Device A, except that TcTA was deposited instead of NPB, and tris(1-phenylpyridine)(acetylacetonate)iridium (III) ("Ir(ppy)₃") (10 wt %) was co-deposited as an emissive layer with Host-2 host material at about 0.01 nm/s and about 0.10 nm/s, respectively, to make the appropriate thickness ratio (about 30 nm).

Each individual device has an area of about 0.16 cm².

Figure 3:
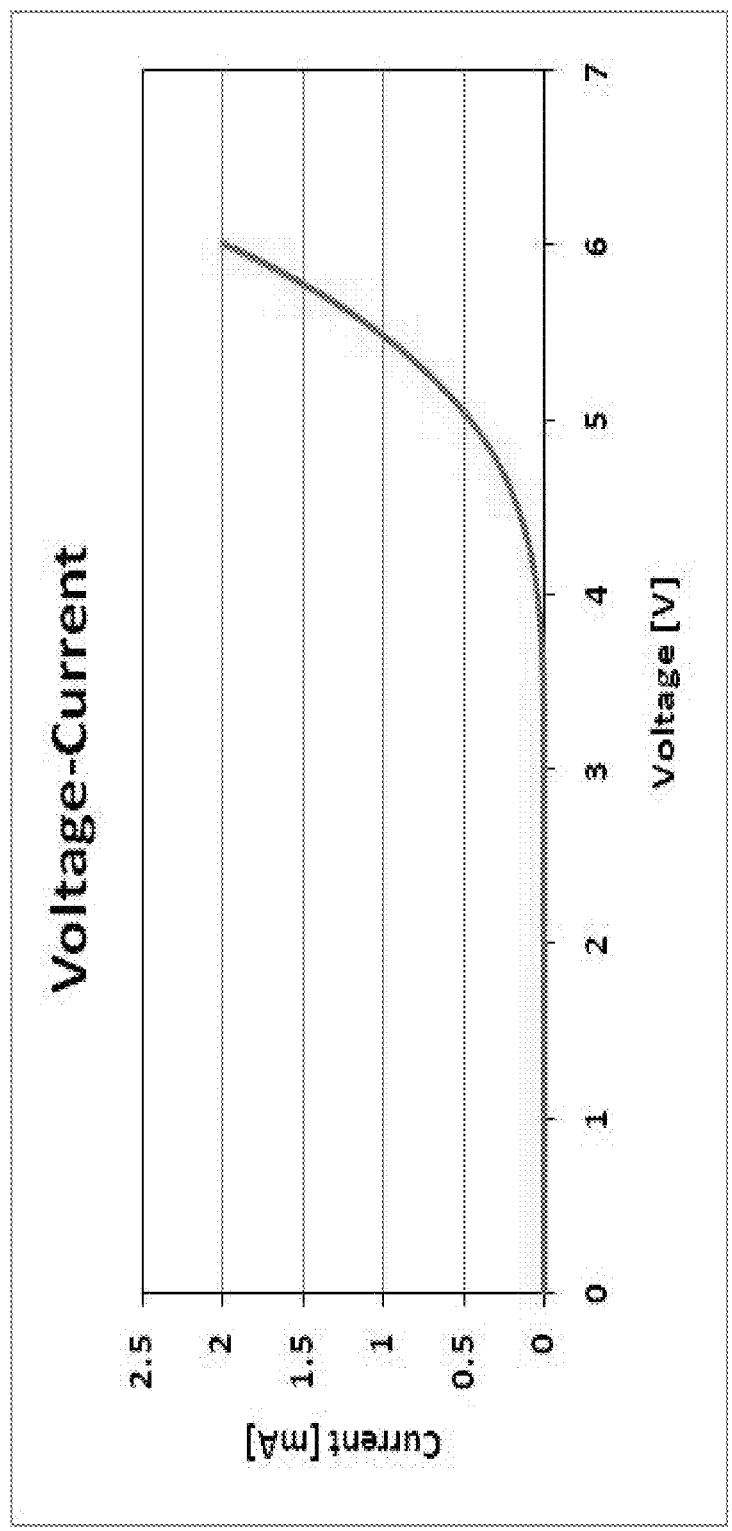
FIG. 3 is a current density versus voltage plot of an embodiment of the light-emitting device incorporating an embodiment of a compound described herein.
Figure 4:
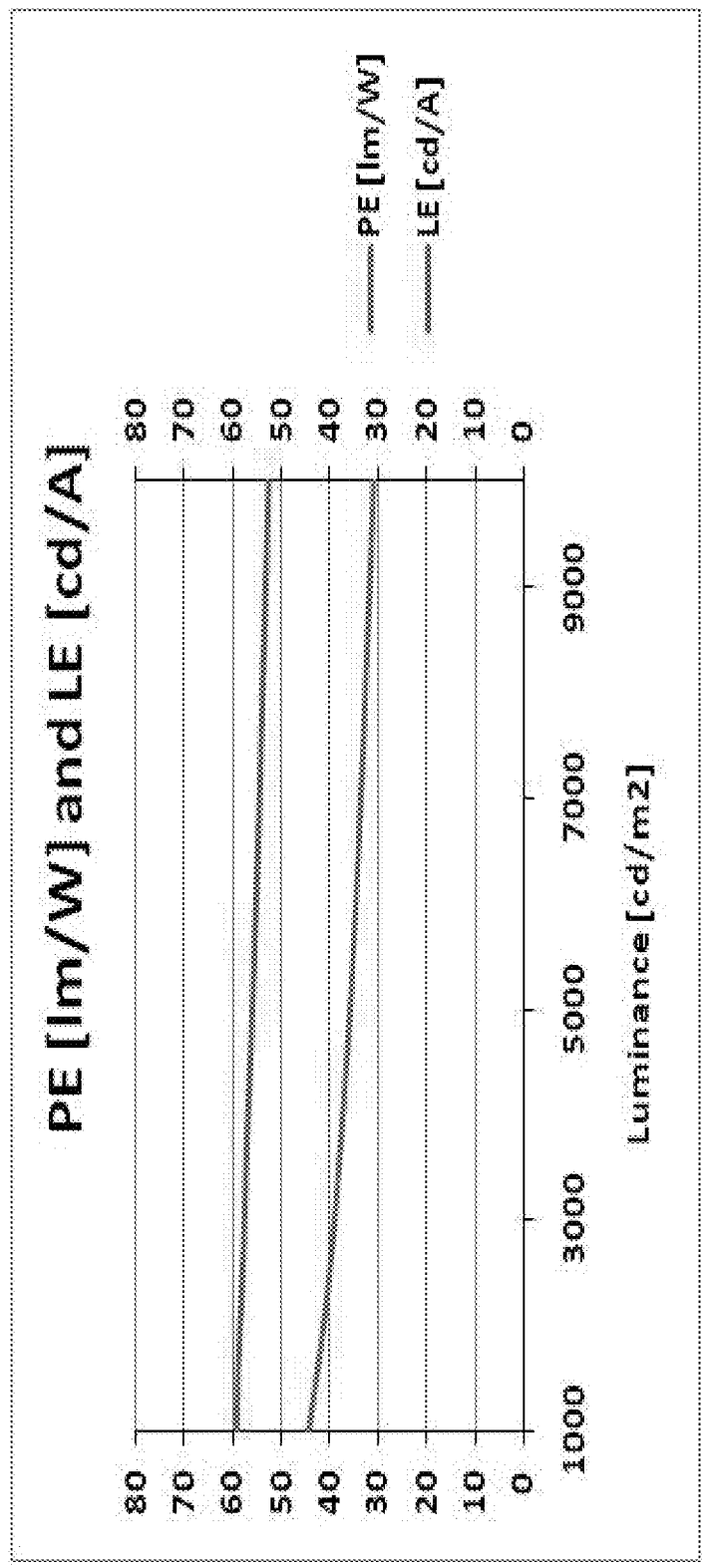
FIG. 4 is a current density versus voltage plot of an embodiment of the light-emitting device incorporating an embodiment of a compound described herein.

Device Performance of Device B was evaluated by measuring the current density and luminance as a function of the driving voltage, as shown in FIG. 3. The turn-on voltage for the device was about 4.17 V and 5.34 V at about 1,000 cd/m² and 10,000 cd/m², respectively. The luminous efficiency (44 lm/W) and power efficiency (60 cd/A) of the device at 1000 cd/m² were determined as a function of luminescence (FIG. 4). A device efficiency of 17% was higher than expected, and demonstrates that Host-2 may be useful as host materials in a light emitting device.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A host compound for use in emissive elements of organic light emitting devices, the compound being represented by a formula:

HT-Ph¹-Ph²-ET wherein Ph¹ and Ph² are independently optionally substituted o-phenylene; and HT is optionally substituted 4-(phenylcarbazolyl)phenyl; and ET is optionally substituted benzimidazol-2-yl, optionally substituted benzimidazol-2-ylphenyl, optionally substituted di(benzimidazol-2-yl)phenyl, optionally substituted benzothiazol-2-ylphenyl, optionally substituted benzoxazol-2-ylphenyl, optionally substituted di(benzoxazol-2-yl)phenyl, optionally substituted 3,3'-bipyridin-5-yl, optionally substituted quinolin-8-yl, optionally substituted quinolin-5-yl, or optionally substituted quinoxalin-5-yl.

2. A host compound for use in emissive elements of organic light emitting devices, the compound being represented by a formula:

HT-$Ph^1$-$Ph^2$-ET wherein $Ph^1$ and $Ph^2$ are independently optionally substituted o-phenylene;

HT is optionally substituted phenylcarbazolyl, optionally substituted (phenylcarbazolyl)phenyl, optionally substituted 4-(phenylnaphthylamino)phenyl, or optionally substituted 4-(diphenylamino)phenyl; and wherein ET is optionally substituted di(benzimidazol-2-yl)phenyl.

3. A host compound for use in emissive elements of organic light emitting devices, the compound being represented by a formula:

HT-$Ph^1$-$Ph^2$-ET wherein $Ph^1$ and $Ph^2$ are independently optionally substituted o-phenylene;

HT is optionally substituted phenylcarbazolyl, optionally substituted (phenylcarbazolyl)phenyl, optionally substituted 4-(phenylnaphthylamino)phenyl, or optionally substituted 4-(diphenylamino)phenyl; and wherein ET is optionally substituted di(benzoxazol-2-yl)phenyl.

* * * * *